(12) United States Patent
Hirata et al.

(10) Patent No.: US 9,173,849 B2
(45) Date of Patent: Nov. 3, 2015

(54) SOLID PHARMACEUTICAL COMPOSITION

(75) Inventors: Kazuhiro Hirata, Osaka (JP); Junya Nomura, Osaka (JP); Yutaka Tanoue, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 596 days.

(21) Appl. No.: 12/998,167

(22) PCT Filed: Sep. 25, 2009

(86) PCT No.: PCT/JP2009/066690
§ 371 (c)(1),
(2), (4) Date: May 27, 2011

(87) PCT Pub. No.: WO2010/035806
PCT Pub. Date: Apr. 1, 2010

(65) Prior Publication Data
US 2011/0229567 A1    Sep. 22, 2011

Related U.S. Application Data

(60) Provisional application No. 61/100,108, filed on Sep. 25, 2008.

(51) Int. Cl.
| | | |
|---|---|---|
| A61K 31/455 | (2006.01) | |
| A61K 31/4245 | (2006.01) | |
| A61K 9/20 | (2006.01) | |
| A61P 9/12 | (2006.01) | |
| A61P 9/00 | (2006.01) | |
| A61K 31/4184 | (2006.01) | |
| A61K 31/4422 | (2006.01) | |
| A61K 45/06 | (2006.01) | |

(52) U.S. Cl.
CPC ............ *A61K 9/2086* (2013.01); *A61K 9/2054* (2013.01); *A61K 31/4184* (2013.01); *A61K 31/4422* (2013.01); *A61K 45/06* (2013.01)

(58) Field of Classification Search
CPC .. A61K 2300/00; A61K 45/06; A61K 9/2086
USPC ................ 424/464; 514/364, 356, 381, 210.2
See application file for complete search history.

(56) References Cited

U.S. PATENT DOCUMENTS

| | | | |
|---|---|---|---|
| 5,243,054 A | 9/1993 | Naka et al. | |
| 5,354,766 A | 10/1994 | Naka et al. | |
| 5,583,141 A | 12/1996 | Naka et al. | |
| 5,656,650 A | 8/1997 | Weinstock | |
| 5,703,110 A | 12/1997 | Naka et al. | |
| 5,721,263 A * | 2/1998 | Inada et al. ................... | 514/381 |
| 5,736,555 A | 4/1998 | Naka et al. | |
| 5,883,111 A | 3/1999 | Naka et al. | |
| 5,958,961 A | 9/1999 | Inada et al. | |
| 5,962,491 A | 10/1999 | Naka et al. | |
| 6,100,252 A | 8/2000 | Naka et al. | |
| 6,228,874 B1 | 5/2001 | Inada et al. | |
| 6,348,481 B2 | 2/2002 | Inada et al. | |
| 6,420,405 B2 | 7/2002 | Inada et al. | |
| 6,459,014 B1 * | 10/2002 | Chmielewski et al. ........ | 604/360 |
| 7,157,584 B2 | 1/2007 | Kuroita et al. | |
| 7,413,751 B2 | 8/2008 | Devane et al. | |
| 7,572,920 B2 | 8/2009 | Kuroita et al. | |
| 2002/0143024 A1 | 10/2002 | Murugesan et al. | |
| 2004/0106833 A1 | 6/2004 | San et al. | |
| 2004/0127515 A1 | 7/2004 | Murugesan et al. | |
| 2004/0170687 A1 | 9/2004 | Hurd et al. | |
| 2004/0219208 A1 | 11/2004 | Kawamura et al. | |
| 2005/0065148 A1 | 3/2005 | Feng et al. | |
| 2005/0070530 A1 | 3/2005 | Feng et al. | |
| 2005/0070531 A1 | 3/2005 | Feng et al. | |
| 2005/0070535 A1 | 3/2005 | Feng et al. | |
| 2005/0070706 A1 | 3/2005 | Feng et al. | |
| 2005/0075330 A1 | 4/2005 | Feng et al. | |
| 2005/0187269 A1 * | 8/2005 | Kuroita et al. ................ | 514/364 |
| 2006/0134206 A1 | 6/2006 | Iyer et al. | |
| 2006/0177506 A1 * | 8/2006 | Yanai et al. ................... | 424/468 |
| 2008/0279942 A1 | 11/2008 | Hamaura et al. | |
| 2009/0012132 A1 | 1/2009 | Nonomura | |
| 2009/0042863 A1 | 2/2009 | Takeuchi et al. | |
| 2009/0054502 A1 | 2/2009 | Kuroita et al. | |
| 2009/0208584 A1 * | 8/2009 | Yoshinari et al. ............. | 424/499 |
| 2009/0214664 A1 | 8/2009 | Ohm et al. | |
| 2009/0270464 A1 | 10/2009 | Kuroita et al. | |
| 2010/0092551 A1 | 4/2010 | Nakamura et al. | |
| 2010/0121071 A1 | 5/2010 | Yoneyama et al. | |
| 2010/0136127 A1 | 6/2010 | Yamamoto et al. | |
| 2012/0172401 A1 | 7/2012 | Kuroita et al. | |

FOREIGN PATENT DOCUMENTS

| | | |
|---|---|---|
| CA | 2456034 A1 | 2/2003 |
| EP | 0 520 423 B1 | 12/1992 |
| EP | 0 628 313 A1 | 12/1994 |

(Continued)

OTHER PUBLICATIONS

Wikipedia—Citrate 2014.*
Badawy et al. (Journal of Pharmaceutical Sciences, vol. 96, No. 5, May, pp. 948-959 2007).*
Hasebe et al., "Controlled-release nifedipine and candesartan low-dose combination therapy in patients with essential hypertension: the NICE Combi (Nifedipine and Candesartan Combination) Study," Journal of Hypertension, 2005, 23(2):445-453.
http://www.ub/es/legmh/capitols/sunyenegre.pdf, Sune Negre, Prof. D. Jose M., "Nuevas Aportaciones Galenicas a las formas de Administracion," Formacion Continuada para Farmaceuticos de Hospital, 21 pages, publication date unknown.

(Continued)

*Primary Examiner* — Anna Falkowitz
(74) *Attorney, Agent, or Firm* — Foley & Lardner LLP

(57) ABSTRACT

The present invention provides a solid preparation containing compound (I) or a salt thereof, a pH control agent and a calcium antagonist, which is superior in the dissolution property, stability and the like.

1 Claim, 1 Drawing Sheet

(56) References Cited

FOREIGN PATENT DOCUMENTS

| | | | | |
|---|---|---|---|---|
| JP | 2001-294524 A | | 10/2001 | |
| JP | WO2006/132440 | * | 12/2006 | ............. A61K 47/38 |
| JP | WO 2007/001067 | * | 1/2007 | ............... A61K 9/50 |
| WO | WO 92/10097 A1 | | 6/1992 | |
| WO | WO 03/035039 A1 | | 5/2003 | |
| WO | WO 2005/009412 A1 | | 2/2005 | |
| WO | WO 2005/016911 A1 | | 2/2005 | |
| WO | WO 2005/080384 A2 | | 9/2005 | |
| WO | WO 2007/001066 A1 | | 1/2007 | |
| WO | WO 2007/001067 A2 | | 1/2007 | |
| WO | WO 2007/003330 A2 | | 1/2007 | |
| WO | WO 2007/074884 A1 | | 7/2007 | |
| WO | WO 2007/097451 A1 | | 8/2007 | |
| WO | WO 2008/093882 A1 | | 8/2008 | |
| WO | WO 2008/123536 A1 | | 10/2008 | |
| WO | WO 2009/011451 A1 | | 1/2009 | |
| WO | WO 2010/013835 A2 | | 2/2010 | |

OTHER PUBLICATIONS http://es.wikipedia.org/wiki/Forma_gal%C3%A9nica, Medicamento, 37 pages, publication date unknown.

http://intranet.comunidadandina.org/documentos/Gacetas/gace722.pdf, Gaceta Oficial del Acuerdo de Cartanega, Oct. 12, 2001, 722:1-40.

http://intranet.comunidadandina.org/Documentos/Procesos/21-ip-2000.doc, Tribunal de Justicial de la Comunidad Andina, Oct. 27, 2000, 17 pages.

http://knol.google.com/k/alejandro-melo-flori%C3%A1n/introducci%C3%B3n-a-la-farmacolog%C3%ADa/3sktw3ldc86j2/53#, Introduccion a la Farmacologia, 16 pages, publication date unknown.

International Search Report mailed Oct. 27, 2009, in PCT/JP2009/066690, 4 pages.

* cited by examiner

SOLID PHARMACEUTICAL COMPOSITION

CROSS-REFERENCE TO RELATED APPLICATIONS

This application is a National Stage application of PCT/JP2009/066690, filed Sep. 25, 2009, which claims priority from Japanese application JP 2009-066690.

TECHNICAL FIELD OF THE INVENTION

The present invention relates to a solid preparation comprising a compound represented by the formula (I) to be shown below, a pH control agent and a calcium antagonist, which is superior in the stability and dissolution property of the compound (I) represented by the formula (I) and the calcium antagonist.

BACKGROUND OF THE INVENTION

It is important that pharmaceutical products be effective and safe. Even if a pharmaceutical product is effective and safe immediately after production, if the drug is easily decomposed or denatured during distribution of the pharmaceutical product, it is not considered to be effective and safe as a pharmaceutical product. Therefore, the stability of the drug is extremely important for pharmaceutical products.

To secure effectiveness and safety of a pharmaceutical product, not only the effectiveness and safety of the active ingredient itself are important but also the properties of the pharmaceutical preparation, such as the drug dissolution property in the body and the like, are extremely important. For example, when dissolution of the drug from the pharmaceutical preparation is too late, the blood concentration of the drug does not reach an effective level, and the expected efficacy may not be sufficiently exhibited. On the other hand, when dissolution of the drug from the pharmaceutical preparation is too fast, the blood concentration of the drug increases sharply, causing a high risk of side effects.

In other words, pharmaceutical products are required to ensure the stability of the drug and a certain level of the drug dissolution, in addition to the effectiveness and safety.

Meanwhile, the drug dissolution property is known to correlate with the solubility thereof. In general, lower solubility of a drug is known to cause slower drug dissolution property.

Incidentally, benzimidazole derivative (I) having a strong angiotensin II receptor antagonistic activity (I)

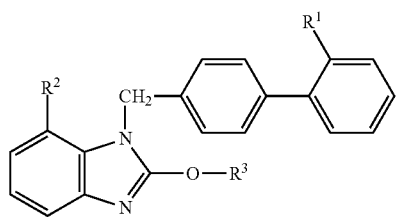

wherein $R^1$ is a monocyclic nitrogen-comprising heterocyclic group having a hydrogen atom that can be deprotonized, $R^2$ is an esterified carboxyl group, and $R^3$ is an optionally substituted lower alkyl, or a salt thereof (hereinafter to be sometimes referred to as compound (I)), particularly, a salt of (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate (patent document 1) is a promising therapeutic drug for hypertension and the like. However, the properties of a pharmaceutical preparation need to be adjusted to stabilize compound (I) because compound (I) is unstable in the neutral pH range, at which pharmaceutical preparations are generally produced. Nevertheless, the solubility of compound (I) is low at the pH range where compound (I) is stable. In addition, a combination drug product composed of compound (I) and active ingredients such as calcium antagonist and the like cannot be easily formulated into, a pharmaceutical preparation superior in the stability and dissolution property due to the difference in chemical properties.

As combination drug product, a combination of a compound having an angiotensin II antagonistic activity and a compound having a calcium antagonistic action (patent document 2) and an oral solid preparation containing acetaminophen obtained by a separating granulation method to suppress the unpleasant taste of acetaminophen and prevent discoloration thereof (patent document 3) are known. However, a combination drug product of compound (I) and a calcium antagonist, which simultaneously achieves stability and solubility, i.e., dissolution property, of the drug has not been known.

CITATION LIST

Patent Literature

[patent document 1] WO2005/080384
[patent document 2] U.S. Pat. No. 5,721,263
[patent document 3] JP-A-2001-294524

SUMMARY OF THE INVENTION

Problems to be Solved by the Invention

A preparation comprising compound (I) and a calcium antagonist is effective for the prophylaxis or treatment of circulatory diseases such as hypertension, cardiac failure, diabetic nephropathy, arteriosclerosis and the like, and has extremely high clinical usefulness.

It is an object of the present invention to provide a solid preparation superior in the stability of compound (I) and a calcium antagonist as well as dissolution property thereof.

Means of Solving the Problems

The present inventors have conducted intensive studies in an attempt to simultaneously achieve the stability of compound (I) in a preparation and the dissolution property thereof from the preparation, and found that the object can be unexpectedly accomplished by the co-presence of a pH control agent and compound (I), and further, by adjusting, with a pH control agent, the pH range of a solid preparation thereof to a pH range in which the solubility of compound (I) becomes low. They have also found that even when compound (I) and a calcium antagonist are used in combination, both of them show superior stability. Moreover, they have found that compound (I) and a calcium antagonist can be further stabilized by separately granulating compound (I) added with a pH control agent and the calcium antagonist, and a preparation more superior in the dissolution property of compound (I) as compared to general granulation preparations can be obtained, which resulted in the completion of the present invention.

Accordingly, the present invention provides the following.
(1) A solid preparation comprising a compound represented by the formula (I)

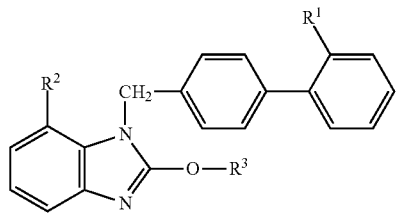

wherein R¹ is a monocyclic nitrogen-comprising heterocyclic group having a hydrogen atom that can be deprotonized, R² is an esterified carboxyl group, and R³ is an optionally substituted lower alkyl, or a salt thereof, a pH control agent and a calcium antagonist.
(2) The solid preparation of the aforementioned (1), wherein the compound represented by the formula (I) or a salt thereof is (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt.
(3) The solid preparation of the aforementioned (1) or (2), wherein the calcium antagonist is amlodipine or an acid addition salt thereof.
(4) The solid preparation of the aforementioned (1) or (2), wherein the calcium antagonist is amlodipine besylate.
(5) The solid preparation of the aforementioned (1), wherein the compound represented by the formula (I) or a salt thereof is (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt and the calcium antagonist is amlodipine besylate.
(6) The solid preparation of the aforementioned (1), wherein the pH control agent has pH 2 to 5.
(7) The solid preparation of the aforementioned (1), wherein the pH control agent is an acidic substance selected from tartaric acid, citric acid, lactic acid, fumaric acid, succinic acid, phosphoric acid, malic acid, ascorbic acid, acetic acid and acidic amino acid, or a salt thereof, or a solvate thereof.
(8) The solid preparation of the aforementioned (1), wherein the pH control agent is monosodium fumarate or a combination of fumaric acid and a sodium ion donor.
(9) A solid preparation comprising a first part comprising a compound represented by the formula (I):

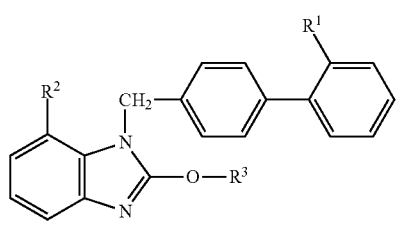

wherein R¹ is a monocyclic nitrogen-comprising heterocyclic group having a hydrogen atom that can be deprotonized, R² is an esterified carboxyl group, and R³ is an optionally substituted lower alkyl, or a salt thereof and a pH control agent, and a second part comprising a calcium antagonist, wherein the first part and the second part are individually granulated.
(10) The solid preparation of the aforementioned (1), which is a multi-layer tablet having a first layer comprised of a first part comprising the compound represented by the formula (I):

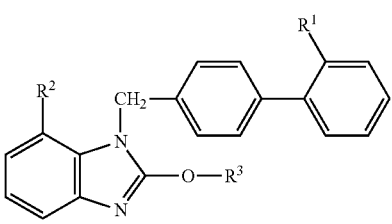

wherein R¹ is a monocyclic nitrogen-comprising heterocyclic group having a hydrogen atom that can be deprotonized, R² is an esterified carboxyl group, and R³ is an optionally substituted lower alkyl, or a salt thereof and the pH control agent, and a second layer comprised of a second part comprising the calcium antagonist.
(11) The solid preparation of the aforementioned (1), wherein the pH control agent is contained in a proportion of 0.01-20 wt % of the preparation.
(12) A method of stabilizing a compound represented by the formula (I):

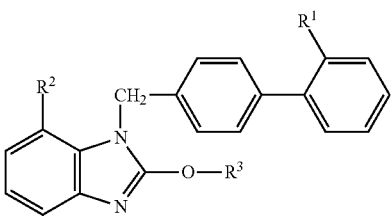

wherein R¹ is a monocyclic nitrogen-comprising heterocyclic group having a hydrogen atom that can be deprotonized, R² is an esterified carboxyl group, and R³ is an optionally substituted lower alkyl, or a salt thereof and a calcium antagonist in a solid preparation, which comprises adding a pH control agent to the solid preparation comprising the compound represented by the formula (I) or a salt thereof, and a calcium antagonist.
(13) A method of improving dissolution of a compound represented by the formula (I) or a salt thereof from a solid preparation, which comprises adding a pH control agent to the solid preparation comprising the compound represented by the formula (I):

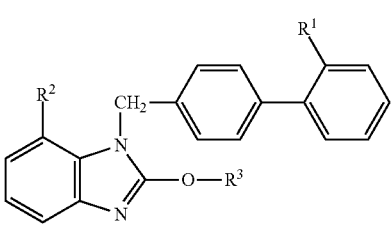

wherein $R^1$ is a monocyclic nitrogen-comprising heterocyclic group having a hydrogen atom that can be deprotonized, $R^2$ is an esterified carboxyl group, and $R^3$ is an optionally substituted lower alkyl, or a salt thereof, and a calcium antagonist; and the like.

DETAILED DESCRIPTION OF THE INVENTION

Figure 1:
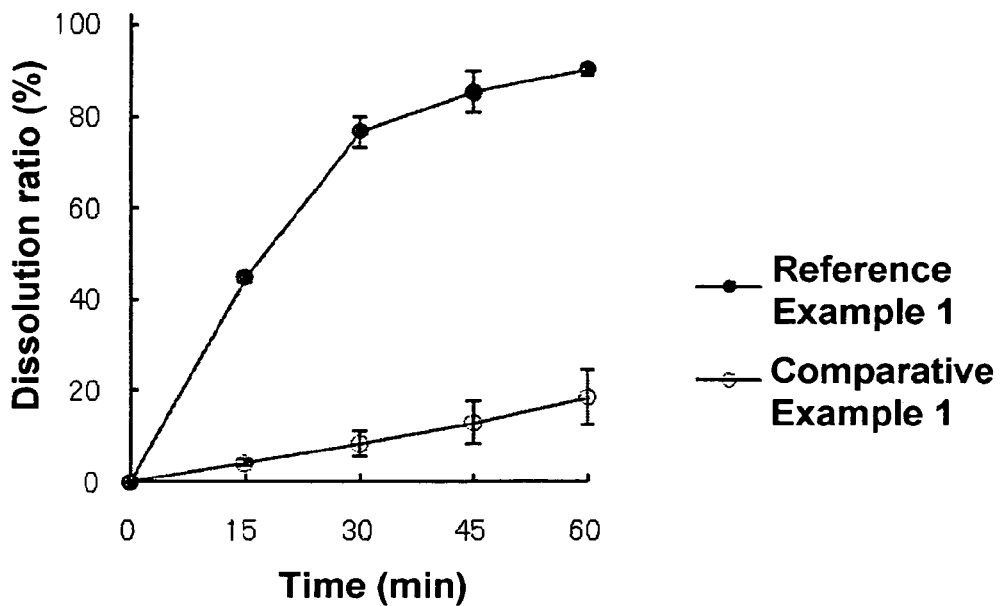
FIG. 1 shows the drug dissolution ratios of the tablets obtained in Reference Example 1 and Comparative Example 1.

The solid preparation of the present invention is explained in detail in the following.

The solid preparation of the present invention comprises compound (I), a pH control agent and a calcium antagonist. The solid preparation of the present invention is superior in the stability of compound (I), as well as superior in the dissolution property of the compound. In addition, it is superior in the stability of the calcium antagonist.

In the aforementioned formula (I), $R^1$ is a monocyclic nitrogen-comprising heterocyclic group having a hydrogen atom that can be deprotonized, such as a tetrazolyl group or a group represented by the formula

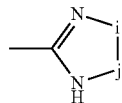

wherein i is —O— or —S—, j is >C=O, >C=S or >S(O)m wherein m is 0, 1 or 2 (e.g., 4,5-dihydro-5-oxo-1,2,4-oxadiazol-3-yl group, etc.) and the like are preferable.

A 4,5-dihydro-5-oxo-1,2,4-oxadiazol-3-yl group includes three tautomers (a', b' and c') represented by the formulas:

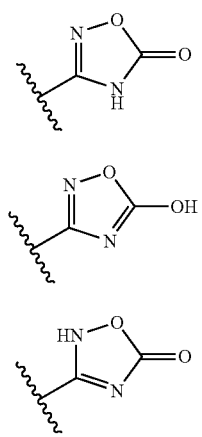

and 4,5-dihydro-5-oxo-1,2,4-oxadiazol-3-yl group includes all of the above-mentioned a', b' and c'.

In the aforementioned formula (I), $R^2$ is an esterified carboxyl group and, for example, preferably a carboxyl group esterified by lower($C_{1-4}$)alkyl optionally substituted by a substituent selected from a hydroxyl group, an amino group, a halogen atom, lower($C_{2-6}$)alkanoyloxy (e.g., acetyloxy, pivaloyloxy, etc.), lower ($C_{4-7}$) cycloalkanoyloxy, (lower ($C_{1-6}$) alkoxy)carbonyloxy (e.g., methoxycarbonyloxy, ethoxycarbonyloxy, etc.), (lower($C_{3-7}$)cycloalkoxy)carbonyloxy (e.g., cyclohexyloxycarbonyloxy, etc.), lower($C_{1-4}$)alkoxy and 5-methyl-2-oxo-1,3-dioxolen-4-yl (e.g., (5-methyl-2-oxo-1,3-dioxolen-4-yl)methoxycarbonyl group, 1-(cyclohexyloxycarbonyloxy)ethoxycarbonyl group) and the like.

In the aforementioned formula (I), $R^3$ is an optionally substituted lower alkyl, and preferably a lower($C_{1-5}$)alkyl optionally substituted by a substituent selected from a hydroxyl group, an amino group, a halogen atom and a lower ($C_{1-4}$) alkoxy group (preferably lower ($C_{2-3}$) alkyl; particularly preferably ethyl).

As a salt of the compound represented by the formula (I), a pharmaceutically acceptable salt can be mentioned and, for example, a salt of a compound represented by the formula (I) with an inorganic base, a salt thereof with an organic base, a salt thereof with an inorganic acid, a salt thereof with an organic acid, a salt thereof with a basic or acidic amino acid and the like can be mentioned. Preferable examples of the salt with an inorganic base include alkali metal salt such as sodium salt, potassium salt and the like; alkaline earth metal salt such as calcium salt, magnesium salt and the like; aluminum salt, ammonium salt and the like. Preferable examples of the salt with an organic base include salts with trimethylamine, triethylamine, pyridine, picoline, ethanolamine, diethanolamine, triethanolamine, dicyclohexylamine, N,N'-dibenzylethylenediamine and the like. Preferable examples of the salt with an inorganic acid include salts with hydrochloric acid, hydrobromic acid, nitric acid, sulfuric acid, phosphoric acid and the like. Preferable examples of the salt with an organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with a basic amino acid include salts with arginine, lysine, ornithine and the like. Preferable examples of the salt with an acidic amino acid include salts with aspartic acid, glutamic acid and the like.

As a compound represented by the formula (I) or a salt thereof, a salt of (5-methyl-2-oxo-1,3-dioxol-4-yl)methyl 2-ethoxy-1-{[2'-(5-oxo-4,5-dihydro-1,2,4-oxadiazol-3-yl) biphenyl-4-yl]methyl}-1H-benzimidazole-7-carboxylate is preferable, and (5-methyl-2-oxo-1,3-dioxol-4-yl)methyl 2-ethoxy-1-{[2'-(5-oxo-4,5-dihydro-1,2,4-oxadiazol-3-yl) biphenyl-4-yl]methyl}-1H-benzimidazole-7-carboxylate potassium salt is particularly preferable.

The salt of a compound represented by the formula (I) may be hydrate or non-hydrate.

In addition, compound (I) may be a solvate including hydrate or a non-solvate.

Compound (I) is preferably crystalline, and preferably has the melting point of 100-250° C., particularly 120-200° C., especially 130-180° C.

Compound (I) is contained in the solid preparation of the present invention in a proportion of 0.1-60 wt %, preferably 1-40 wt %, more preferably 5-30 wt %.

As the pH control agent to be used in the present invention, any pH control agent can be used as long as it can simultaneously achieve the stability of compound (I) in a preparation and dissolution property thereof from the preparation, and is applicable to pharmaceutical products. Plural pH control agents may be used in combination. As the pH control agent to be used in the present invention, the pH control agent showing pH of about 2 to about 5, preferably about 3 to about 5, more preferably about 3 to about 4 is preferably used. For example, an acidic substance such as tartaric acid, citric acid, lactic acid, fumaric acid, phosphoric acid, malic acid, succinic acid, ascorbic acid, acetic acid, acidic amino acid (e.g., glutamic acid, aspartic acid) and the like, inorganic salts of these acidic substances (e.g., alkali metal salt, alkaline earth metal salt, ammonium salt, etc.), salts of these acidic substances with an organic base (e.g., basic amino acid such as lysine, arginine, etc., meglumine, etc.), and a solvate thereof (e.g., hydrate), and the like are used. In addition, the pH control agent simultaneously achieves the stability of calcium antagonists in the preparation and the dissolution property from the preparation.

Here, the pH of the pH control agent is measured under the following conditions. To be precise, it is a pH of a solution or suspension obtained by dissolving or suspending a pH control agent in water at a concentration of 1% w/v at 25° C.

As the pH control agent to be used in the present invention, an acidic substance and a basic substance are combined, and the obtained pH control agent may be adjusted such that the pH of the solution or suspension is about 2 to about 5, preferably about 3 to about 5, more preferably about 3 to about 4, when the combined pH control agent is dissolved or suspended in water at 25° C. at a concentration of 1% w/v. Examples of the acidic substance to be used in combination include, in addition to the acidic substances having a pH of about 2 to about 5 mentioned above and salts thereof, strong acids such as hydrochloric acid, sulfuric acid, phosphoric acid and the like. Examples of the basic substance to be used in combination include inorganic bases (e.g., sodium hydroxide, potassium hydroxide, sodium carbonate, sodium hydrogen carbonate, magnesium carbonate, calcium carbonate, magnesium oxide, ammonia, synthetic hydrotalcite), organic bases (e.g., basic amino acid such as lysine, arginine, etc., meglumine, and the like) and the like.

Furthermore, preferable examples of the pH control agent to be used in the present invention include those whose solutions have a buffering ability at said pH, such as sodium dihydrogen phosphate, monosodium fumarate, a combination of fumaric acid and a sodium ion donor and the like.

As the pH control agent to be used in the present invention, monosodium fumarate or a combination of fumaric acid and sodium ion donor is particularly preferable, and fumaric acid and sodium hydroxide may be used in combination.

The solid preparation of the present invention contains the pH control agent in a proportion of 0.01-20 wt %, preferably 0.05-10 wt %, more preferably 0.1-5 wt %.

Examples of the calcium antagonist in the present invention include manidipine, nifedipine, amlodipine, efonidipine, nicardipine and the like. The calcium antagonist in the present invention also includes salts of the compounds exemplified as the above-mentioned calcium antagonists.

As the calcium antagonist in the present invention, amlodipine or a salt thereof is preferable, amlodipine or an acid addition salt thereof is more preferable, and a salt of amlodipine is further preferable. As the salt of amlodipine, amlodipine besylate, amlodipine maleate and the like are preferable, and amlodipine besylate is more preferable.

The calcium antagonist in the present invention is generally contained in the solid preparation in a proportion of 0.05-60 wt % (appropriately adjusted so that the total of compound (I) and pH control agent will not exceed 100%), preferably 0.1-40 wt %, more preferably 0.5-20 wt %. Specifically, amlodipine (based on free form) is generally contained in a proportion of 0.05-60 wt %, preferably 0.1-40 wt %, more preferably 0.5-20 wt %.

A preferable form of the solid preparation of the present invention is, for example, a preparation wherein compound (I) is (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt and the calcium antagonist is amlodipine besylate.

Examples of the solid preparation of the present invention include solid dosage form suitable for oral administration such as tablets, granules, fine granules, capsules, pills and the like.

Accordingly, the embodiments of the solid preparation of the present invention include the following preparations and the like.
(1) A solid preparation obtained by granulating a mixture of compound (I), a pH control agent and a calcium antagonist (single granulation preparation).
(2) A solid preparation comprising a first part comprising compound (I) and a pH control agent and a second part comprising a calcium antagonist, which is obtained by separately granulating the first part and the second part (separating granulation preparation—single layer tablet).
(3a) A solid preparation obtained by compression molding the first part and the second part, each independently granulated (separating granulation preparation—multi-layer tablet).
(3b) A solid preparation obtained by coating one part with the other part in the individually granulated first part and the second part, (separating granulation preparation—coated tablet).

The solid preparation of the above-mentioned (1) (single granulation preparation) simultaneously achieves dissolution property of each of compound (1) and a calcium antagonist from the preparation and stability thereof due to the addition of a pH control agent. In the solid preparations of the above-mentioned (2), (3a) and (3b) (separating granulation preparations), the dissolution property and stability thereof of each of compound (I) and a calcium antagonist are more improved.

The solid preparation of the above-mentioned (1) can be produced according to a method known per se (e.g., the method described in the General Rules for Preparations, The Japanese Pharmacopoeia 14th Edition).

For example, when tablets are to be prepared, compound (I), a pH control agent, a calcium antagonist, additives and the like are mixed, a binder is added to give granules, a lubricant and the like are added to the granule and the mixture is tableted to give a tablet. Granules and fine granules can also be produced by the method almost similar to that of the tablet.

Capsules can be produced by filling the above-mentioned granules or fine granules in a capsule containing gelatin, hydroxypropylmethylcellulose and the like, or filling the active ingredient together with a filler in a capsule containing gelatin, hydroxypropylmethylcellulose and the like.

For production of a solid preparation, additives conventionally used in the field of pharmaceutical preparations may be added. Examples of the additive include filler, disintegrant, binder, lubricant, colorant, pH control agent, surfactant, stabilizer, acidulant, flavor, glidant and the like. These additives are used in amounts conventionally employed in the field of pharmaceutical preparations.

Examples of the filler include starches such as cornstarch, potato starch, wheat starch, rice starch, partly pregelatinized starch, pregelatinized starch, porous starch and the like; sugar or sugar alcohols such as lactose, fructose, glucose, mannitol (e.g., D-mannitol), sorbitol (e.g., D-sorbitol), erythritol (e.g., D-erythritol), sucrose and the like: and anhydrous calcium phosphate, crystalline cellulose, microcrystalline cellulose, Glycyrrhiza uralensis, sodium hydrogen carbonate, calcium phosphate, calcium sulfate, calcium carbonate, precipitated calcium carbonate, calcium silicate and the like.

Examples of the disintegrant include amino acid, starch, cornstarch, carboxymethylcellulose, calcium carboxymethylcellulose, sodium carboxymethyl starch, carmellose sodium, carmellose calcium, croscarmellose sodium, crospovidone, low-substituted hydroxypropylcellulose, hydroxypropylstarch, sodium carboxymethyl starch and the like.

Examples of the binder include crystalline cellulose (e.g., microcrystalline cellulose), hydroxypropylcellulose, hydroxypropylmethylcellulose, polyvinylpyrrolidone, gelatin, starch, gum arabic powder, tragacanth, carboxymethylcellulose, sodium alginate, pullulan, glycerol and the like.

Preferable examples of the lubricant include magnesium stearate, stearic acid, calcium stearate, talc (purification talc), sucrose esters of fatty acids, sodium stearyl fumarate and the like.

Examples of the colorant include food colors such as Food Color Yellow No. 5, Food Color Red No. 2, Food Color Blue No. 2 and the like, food lake colors, red ferric oxide and the like.

Examples of the surfactant include sodium lauryl sulfate, polysorbate 80, polyoxyethylene(160)polyoxypropylene(30) glycol and the like.

Examples of the stabilizer include tocopherol, tetrasodium edetate, nicotinamide, cyclodextrins and the like.

Examples of the acidulant include ascorbic acid, citric acid, tartaric acid, malic acid and the like.

Examples of the flavor include menthol, peppermint oil, lemon oil, vanillin and the like.

Examples of the glidant include light anhydrous silicic acid, hydrated silicon dioxide and the like.

The above-mentioned additives may be used in a mixture of two or more kinds thereof at an appropriately ratio.

The solid preparation of the above-mentioned (2) comprises the first part and the second part, which are individually granulated, and can be produced by a method known per se.

In the solid preparation of the above-mentioned (2), the first part of the present invention is a part (composition) comprising compound (I) and a pH control agent.

In the present invention, the pH control agent is used in an amount of preferably 0.01-20 parts by weight, more preferably 0.05-10 parts by weight, further preferably 0.1-5 parts by weight, per 100 parts by weight of the above-mentioned first part.

The weight ratio of compound (I) to pH control agent (compound (I):pH control agent) is preferably 0.1-50:1, more preferably 1-30:1, further preferably 5-25:1.

The above-mentioned first part is not limited as long as it has a shape and size permitting formation of a solid preparation together with the below-mentioned second part.

The above-mentioned first part may further contain additives conventionally used in the field of pharmaceutical preparations. As the additives, those similar to the aforementioned are used.

The above-mentioned first part can be produced by mixing and granulating compound (I) and a pH control agent, together with the above-mentioned additives as necessary according to a method known per se.

The above-mentioned first part preferably contains compound (I) (preferably, (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt, hereinafter compound A); a pH control agent (preferably fumaric acid and sodium hydroxide); a filler (preferably mannitol and crystalline cellulose); and a binder (preferably hydroxypropylcellulose).

In the present invention, the second part (composition) contains a calcium antagonist.

The above-mentioned second part is not limited as long as it has a shape and size permitting formation of a solid preparation together with the aforementioned first part.

The above-mentioned second part may further contain additives conventionally used in the field of pharmaceutical preparations. As the additives, those similar to the aforementioned are used.

Specifically, it contains a calcium antagonist (preferably amlodipine besylate); a filler (preferably mannitol and crystalline cellulose); and a binder (preferably hydroxypropylcellulose).

The above-mentioned second part can be produced by mixing and granulating a calcium antagonist together with the above-mentioned additives as necessary according to a method known per se.

The calcium antagonist is used in an amount of preferably 0.1-60 parts by weight, more preferably 0.5-40 parts by weight, further preferably 1-30 parts by weight, per 100 parts by weight of the above-mentioned second part.

The weight ratio of the second part to the first part (second part:first part) in the solid preparation of the present invention is preferably 0.03-10:1, more preferably 0.1-5:1, further preferably 0.3-3:1.

A single layer tablet produced by mixing individually granulated first and second parts with additives conventionally used in the field of pharmaceutical preparations, and then compressing the mixture is also encompassed in the solid preparation of the present invention. A capsule produced by filling the above-mentioned single layer tablet in a capsule (e.g., hydroxypropylmethylcellulose capsule) is also encompassed in the solid preparation of the present invention.

In addition, a capsule produced by directly filling the first part and the second part, which are separately granulated, or together with the above-mentioned additives in a capsule (e.g., hydroxypropylmethylcellulose capsule) is also encompassed in the solid preparation of the present invention.

The solid preparation of the above-mentioned (3a) can be produced by individually granulating the first part and the second part and compression molding these parts. The solid preparation of the above-mentioned (3b) can be produced by individually granulating the first part and the second part and coating one of them with the other.

Specific examples of the above-mentioned solid preparation (3b) include [1] coated tablet (A) comprising an inner core comprised of the first part and an outer layer comprised of the second part; and [2] coated tablet (B) comprising an inner core comprised of the second part and an outer layer comprised of the first part. Specific examples of the above-mentioned solid preparation (3a) include [3] a multi-layer tablet having a first layer comprised of the first part and a second layer comprised of the second part.

The inner core comprised of the first part can be produced by, for example, granulating compound (I) and a pH control agent together with additives as necessary. In addition, an operation such as drying, sieving, compression and the like may be performed where necessary after granulation.

The outer layer comprised of the second part can be produced by granulating a calcium antagonist (e.g., amlodipine or a salt thereof) together with additives as necessary.

The coating is performed by, for example, compression, coating and the like. In addition, the additive is preferably a binder and the like.

During production of coated tablet (A), an inactive intermediate layer may be formed between an inner core and an outer layer so as to prevent a direct contact between them. The intermediate layer contains, for example, the following coating base and coating additives. The intermediate layer preferably contains a water-soluble film coating base and a glidant.

The above-mentioned coated tablet (B) can be produced in the same manner as in tablet (A) except that the second part is used as an inner core and the first part is used as an outer layer.

The multi-layer tablet in the present invention is a solid preparation comprised of a first part comprising a compound represented by the formula (I) or a salt thereof and a pH control agent, and a second part comprising a calcium antagonist, which has a first layer comprised of the first part and a second layer comprised of the second part.

The multi-layer tablet in the present invention is not particularly limited as long as the first layer comprised of the first part and the second layer comprised of the second part are integrally formed.

Moreover, the multi-layer tablet in the present invention may have an inactive intermediate layer between the first layer and the second layer.

When the multi-layer tablet of the present invention has such an intermediate layer, the adverse influences (decreased preservation stability such as time-course decomposition of active ingredients, lowered effectiveness and the like, decreased dissolution stability such as time-course changes in dissolution pattern of active ingredients and the like, and so on) produced by interaction between the active ingredients can be more effectively suppressed.

The multi-layer tablet can be produced, for example, according to the following production steps.

Compound (I) and a pH control agent are mixed with additives as necessary, the obtained mixture is granulated to give the first part. Operations such as drying, sieving and the like may be performed where necessary after the granulation. Then, the first part is mixed with additives as necessary to give the first layer.

Thereafter, a calcium antagonist is granulated with additives as necessary to give the second part. The second part is mixed with additives as necessary to give the second layer. The second layer is put on the above-mentioned first layer and compressed (preferably tableted).

In this case, an inactive intermediate layer may be formed between respective layers to avoid direct contact between them. The intermediate layer contains, for example, the above-mentioned filler, disintegrant, binder, lubricant, colorant and the like.

A capsule produced by filling the above-mentioned coated tablet (A) or (B) or multi-layer tablet in a capsule (e.g., hydroxypropylmethylcellulose capsule) is also encompassed in the solid preparation of the present invention.

Moreover, a film coated preparation produced by film coating the solid preparation of the above-mentioned (1), (2), (3a) and (3b) with a following coating base and additives for coating is also encompassed in the solid preparation of the present invention.

Preferable examples of the coating base include a sugar coating base, a water-soluble film coating base, an enteric film coating base, a sustained-release film coating base and the like.

As the sugar coating base, sucrose is used. Furthermore, one or more kinds selected from talc, precipitated calcium carbonate, gelatin, gum arabic, pullulan, Carnauba wax and the like may be used in combination.

Examples of the water-soluble film coating base include cellulose polymers such as hydroxypropylcellulose [e.g., grades: L, SL, SL-T, SSL (trade name); Nippon Soda Co., Ltd.], hydroxypropylmethylcellulose [e.g., TC-5 (grades: MW, E, EW, R, RW) (trade name); Shin-Etsu Chemical Co., Ltd.], hydroxyethylcellulose, methylhydroxyethylcellulose and the like; synthetic polymers such as polyvinylacetal diethylaminoacetate, aminoalkylmethacrylate copolymer E [Eudragit E (trade name)], polyvinylpyrrolidone and the like; polysaccharides such as pullulan and the like; and so on.

Examples of the enteric film coating base include cellulose polymers such as hydroxypropylmethylcellulose phthalate, hydroxypropylmethylcellulose acetate succinate, carboxymethylethylcellulose, cellulose acetate phthalate and the like; acrylic acid polymers such as methacrylic acid copolymer L [Eudragit L (trade name)], methacrylic acid copolymer LD [Eudragit L-30D55 (trade name)], methacrylic acid copolymer S [Eudragit S (trade name)] and the like; naturally occurring substances such as shellac and the like; and so on.

Examples of the sustained-release film coating base include cellulose polymers such as ethylcellulose and the like; acrylic acid polymers such as aminoalkylmethacrylate copolymer RS [Eudragit RS (trade name)], ethyl acrylate-methyl methacrylate copolymer suspension [Eudragit NE (trade name)] and the like; and so on.

Preferable examples of the coating additives include light protecting agents such as titanium oxide and the like, glidants such as talc and the like, and/or colorants such as red ferric oxide, yellow ferric oxide and the like; plasticizers such as polyethylene glycol [e.g., macrogol 6000 (trade name)], triethyl citrate, castor oil, polysorbates and the like; organic acids such as citric acid, tartaric acid, malic acid, ascorbic acid and the like; and so on.

Moreover, the solid preparation of the present invention may have a distinguishable embossing or printed letters, or a scored line for division.

The solid preparation of the present invention is preferably film-coated from the aspects of easy administration, mechanical strength and the like.

The operations such as mixing, compression, coating and the like in the above-mentioned production step are performed according to the methods conventionally used in the pharmaceutical field.

For mixing, for example, blending machines such as a V-type mixer, a tumbler mixer and the like; and granulator such as a high speed mixer granulator, a fluid bed granulator, an extrusion granulator, a roller compactor and the like are used.

The compression is performed using, for example, a single stroke tableting machine, a rotary tableting machine and the like.

When compression is performed using a single stroke tableting machine, a rotary tableting machine and the like, it is generally preferable to employ a tableting pressure of 1-20 $KN/cm^2$ (preferably 5-15 $KN/cm^2$), and further, a taper cutting die to prevent capping.

The coating is performed using, for example, a film coating apparatus and the like.

The solid preparation of the present invention can be safely used as a medicine for mammals (e.g., human, dog, rabbit, rat, mouse, etc.).

The solid preparation of the present invention can be safely administered orally or parenterally (e.g., rectally).

While the dose of compound (I) to patients is determined in consideration of age, body weight, general health condition, sex, diet, administration time, clearance rate, combination of drugs and the like, as well as the severity of the disease for which the patient is undergoing treatments, the daily dose is about 0.05-500 mg, preferably 0.1-100 mg, for an adult (body weight 60 kg).

While the dose of a calcium antagonist to patients is is determined in consideration of age, body weight, general health condition, sex, diet, administration time, clearance rate, combination of drugs and the like, as well as the severity of the disease for which the patient is undergoing treatments, the daily dose of amlodipine (based on free form) is about 1-50 mg, preferably 2.5-10 mg, for an adult (body weight 60 kg).

Since compound (I) normalizes intracellular insulin information transduction mechanism, which is the main cause of insulin resistance, reduces the insulin resistance and enhances insulin action, and provides a glucose tolerance-improving effect, it can be used as an agent for improving or preventing and/or treating a disease involving insulin resistance in mammals (e.g., human, monkey, cat, swine, horse, bovine, mouse, rat, guinea pig, dog, rabbit and the like). Examples of such diseases include insulin resistance, impaired glucose tolerance; diabetes such as non-insulin dependent diabetes, type II diabetes, type II diabetes associated with insulin resistance, type II diabetes associated with impaired glucose tolerance and the like; various complications such as hyperinsulinemia, hypertension associated with insulin resistance, hypertension associated with impaired glucose tolerance, hypertension associated with diabetes (e.g., type II diabetes and the like), hypertension associated with hyperinsulinemia, insulin resistance associated with hypertension, impaired glucose tolerance associated with hypertension, diabetes associated with hypertension, and hyperinsulinemia associated with hypertension, diabetic complications [e.g., microangiopathy, diabetic neuropathy, diabetic nephropathy, diabetic retinopathy, diabetic cataract, macroangiopathy, osteopenia, diabetic hyperosmolar coma, infectious diseases (e.g., respiratory infection, urinary tract infection, gastrointestinal infection, dermal soft tissue infection, inferior limb infection etc.), diabetic gangrene, xerostomia, lowered sense of hearing, diabetic cerebrovascular disease, diabetic peripheral circulatory disturbance, diabetic hypertension and the like], diabetic cachexia and the like can be mentioned. Moreover, compound (I) can also be used for the treatment of patients with diabetes, who shows a normal high blood pressure.

Since compound (I) has a strong angiotensin II antagonistic action, moreover, it is useful as a drug for the prophylaxis or treatment of a disease developed by (or a disease whose onset is promoted by) constriction and growth of blood vessel or organ disorder, which is expressed via angiotensin II receptor, the presence of angiotensin II, or a factor induced by the presence of angiotensin II, in mammals (e.g., human, monkey, cat, swine, horse, bovine, mouse, rat, guinea pig, dog, rabbit and the like).

Examples of such diseases include hypertension, circadian blood pressure abnormality, heart diseases (e.g., cardiac hypertrophy, acute cardiac failure, chronic cardiac failure including congestive cardiac failure, cardiaomyopathy, angina, myocarditis, atrial fibrillation, arrhythmia, tachycardia, myocardial infarction etc.), cerebrovascular disorders (e.g., asymptomatic cerebrovascular disorder, transient cerebral ischemic attack, cerebral apoplexy, cerebrovascular dementia, hypertensive encephalopathy, cerebral infarction, subarachnoid hemorrhage etc.), cerebral edema, cerebral circulatory disorder, recurrence and sequela of cerebrovascular disorders (e.g., neurotic symptom, psychic symptom, subjective symptom, disorder in daily living activities etc.), ischemic peripheral circulation disorder, myocardial ischemia, venous insufficiency, progression of cardiac insufficiency after myocardial infarction, renal diseases (e.g., nephritis, glomerulonephritis, glomerulosclerosis, chronic renal failure, acute renal failure, thrombotic vasculopathy, complication of dialysis, organ disorder including nephropathy by radiation irradiation etc.), arteriosclerosis including atherosclerosis (e.g., aneurysm, coronary atherosclerosis, cerebral arterial sclerosis, peripheral arterial sclerosis etc.), vascular hypertrophy, vascular hypertrophy or occlusion and organ disorders after intervention (e.g., percutaneous coronary angioplasty, stenting, coronary angioscopy, intravascular ultrasound, intracoronary thrombolysis etc.), vascular reocclusion and restenosis after bypass surgery, polycythemia, hypertension, organ disorder and vascular hypertrophy after transplantation, rejection after transplantation, ocular diseases (e.g., glaucoma, ocular hypertension etc.), thrombosis, multiple organ disorder, endothelial function disorder, hypertensive tinnitus, other cardiovascular diseases (e.g., deep vein thrombosis, obstructive peripheral circulatory diturbance, arteriosclerosis obliterans, thromboangiitis obliterans, ischemic cerebral circulatory disorder, Raynaud's disease, Berger disease etc.), metabolic and/or nutritional disorders (e.g., obesity, hyperlipidemia, hypercholesterolemia, hyperuricacidemia, hyperkalemia, hypernatremia etc.), neurodegenerative diseases (e.g., Alzheimer's disease, Parkinson's disease, amyotrophic lateral sclerosis, AIDS encephalopathy etc.), central nervous system disorders (e.g., damages such as cerebral hemorrhage and cerebral infarction, and sequela and complication thereof, head injury, spinal injury, cerebral edema, sensory malfunction, sensory functional disorder, autonomic nervous system disorder, autonomic nervous system malfunction, multiple sclerosis etc.), dementia, defects of memory, disorder of consciousness, amnesia, anxiety symptom, catatonic symptom, discomfort mental state, psychopathies (e.g., depression, epilepsy, alcoholism etc.), inflammatory diseases (e.g., arthritis such as chronic rheumatoid arthritis, osteoarthritis, rheumatoid myelitis, periostitis etc.; inflammation after operation or injury; remission of swelling; pharyngitis; cystitis; pneumonia; atopic dermatitis; inflammatory intestinal diseases such as Crohn's disease, ulcerative colitis etc.; meningitis; inflammatory ocular disease; pulmonary sarcoidosiss such as pneumonia, pulmonary silicosis, pulmonary sarcoidosis, pulmonary tuberculosis etc.), allergic diseases (e.g., allergic rhinitis, conjunctivitis, gastrointestinal allergy, pollinosis, anaphylaxis etc.), chronic obstructive pulmonary disease, interstitial pneumonia, pneumocytis carinni pneumonia, collagen diseases (e.g., systemic lupus erythematosus, scleroderma, polyarteritis etc.), hepatic diseases (e.g., non-alcoholic steatohepatitis (NASH), non-alcoholic fatty liver diseases (NAFLD), hepatitis including chronic hepatitis, hepatic cirrhosis etc.), portal hypertension, digestive system disorders (e.g., gastritis, gastric ulcer, gastric cancer, gastric disorder after operation, dyspepsia, esophageal ulcer, pancreatitis, colon polyp, cholelithiasis, hemorrhoidal disease, varices ruptures of esophagus and stomach etc.), blood and/or myelopoietic diseases (e.g., erythrocytosis, vascular purpura, autoimmune hemolytic anemia, disseminated intravascular coagulation syndrome, multiple myelopathy etc.), bone diseases (e.g., fracture, refracture, osteoporosis, osteomalacia, Paget's disease of bone, sclerosing myelitis, chronic rheumatoid arthritis, joint tissue dysfunction and the like caused by knee osteoarthritis and diseases similar to these), solid tumor, tumors (e.g., malignant melanoma, malignant lymphoma, cancer of digestive organs (e.g., stomach, intestine etc.) etc.), cancer and cachexia following cancer, metastasis cancer, endocrinopathy (e.g., Addison's disease, Cushing's syndrome, pheochromocytoma, primary aldosteronism etc.), Creutzfeldt-Jakob disease, urinary organ and/or male genital diseases (e.g., cystitis, prostatic hypertrophy, prostatic cancer, sex infectious disease etc.), female disorders (e.g., climacteric disorder, gestosis, endometriosis, hysteromyoma, ovarian disease, breast disease, sex infectious disease etc.), disease relating to environment and occupational factors (e.g., radiation hazard, hazard by ultraviolet, infrared or laser beam, altitude sickness etc.), respiratory diseases (e.g., cold syndrome, pneumonia, asthma, pulmonary hypertension, pulmonary thrombosis and pulmonary embolism etc.), infectious diseases (e.g., viral infectious diseases with cytomegalovirus, influenza virus, herpes virus etc., rickettsiosis, bacterial infectious disease etc.), toxemias (e.g., sepsis, septic shock, endotoxin shock, Gram-negative sepsis, toxic shock syndrome etc.), otorhinolaryngological diseases (e.g., Meniere's syndrome, tinnitus, dysgeusia, vertigo, disequilibrium, dysphagia etc.), skin diseases (e.g., keloid, Hemangioma, psoriasis etc.), intradialytic hypotension, myasthenia gravis, systemic diseases such as chronic fatigue syndrome and the like, and the like.

Since compound (I) can maintain a certain hypotensive action through day and night, the dose and frequency can be reduced, and moreover, elevation of blood pressure before and after awakening, which is particularly problematic in patients with hypertension, can be suppressed more effectively.

In addition, continuous long-term suppression of the action of angiotensin II by compound (I) results in the improvement or suppression of promotion of disorder or abnormality in the biofunction and physiological action, that causes adult disorders and various diseases linked with aging and the like, which in turn leads to the primary and secondary prophylaxis of diseases or clinical conditions caused thereby or suppression of the progression thereof. As the disorder or abnormality in the biofunction and physiological action, for example, disorder or abnormality in automatic controlling capability of cerebral circulation and/or renal circulation, disorder of circulation (e.g., peripheral, cerebral, microcirculation etc.), disorder of blood-brain-barrier, salt sensitivity, abnormal state of coagulation and fibrinolysis system, abnormal state of blood and blood cell components (e.g., accentuation of platelet aggregation action, malfunction of erythrocyte deformability, accentuation of leukocyte adhesiveness, rise of blood viscosity etc.), production and function accentuation of growth factor and cytokines (e.g., PDGF, VEGF, FGF, interleukin, TNF-α, MCP-1 etc.), accentuation of production and infiltration of inflammatory cells, accentuation of production of free radical, liposteatosis accentuation, endothelial function disorder, endothelium, cell and organ dysfunction, edema, cell morphogenesis change of smooth muscle etc. (morphogenesis to proliferation type etc.), production and function accentuation of vasoactive substance and thrombosis inducers (e.g., endothelin, thromboxane $A_2$ etc.), abnormal constriction of blood vessel etc., metabolic disorder (e.g., serum lipid abnormalities, dysglycemia etc.), abnormal growth of cell etc., angiogenesis (including abnormal vasculogenesis during abnormal capillary reticular formation in adventitia of arteriosclerotic lesion) and the like can be mentioned. Among them, compound (I) can be used as an agent for the primary and secondary prophylaxis or treatment of organ disorders associated with various diseases (e.g., cerebrovascular disorder and organ disorder associated therewith, organ disorder associated with cardiovascular disease, organ disorder associated with diabetes, organ disorder after intervention etc.). In particular, since compound (I) has an activity of inhibiting proteinuria, the compound can be used as an agent for protecting kidney. Therefore, compound (I) can be advantageously used when the patients with insulin resistance, impaired glucose tolerance, diabetes or hyperinsulinemia have concurrently developed the above-mentioned diseases or clinical condition.

Since compound (I) has an activity of inhibiting body weight gain, it can be used as a body weight gain inhibitor to mammals. Target mammals may be any mammals of which body weight gain is to be avoided. The mammals may have a risk of body weight gain genetically or may be suffering from lifestyle-related diseases such as diabetes, hypertension and/or hyperlipidemia and the like. The body weight gain may be caused by excessive feeding or diet without nutrient balance, or may be derived from combination drug (e.g., agents for enhancing insulin sensitivity having PPARγ-agonistic activity such as troglitazone, rosiglitazone, englitazone, ciglitazone, pioglitazone and the like). In addition, body weight gain may be preliminary to obesity, or may be body weight gain of obesity patients. Here, obesity is defined that BMI (body mass index; body weight (kg)/[height (m)]$^2$) is not less than 25 for Japanese (criterion by Japan Society for the Study of Obesity), or not less than 30 for westerner (criterion by WHO).

In addition, compound (I) can be used as an agent for the prophylaxis or treatment of hypertension associated with obesity or an agent for the prophylaxis or treatment of obesity associated with hypertension.

As for the diagnostic criteria of diabetes, the Japan Diabetes Society reported new diagnostic criteria in 1999.

According to the report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, ADA (American Diabetes Association) reported new diagnostic criteria of diabetes in 1997 and WHO in 1998.

According to these reports, diabetes is a condition showing a fasting blood glucose level (glucose concentration of intravenous plasma) of not less than 126 mg/dl, or a 75 g oral glucose tolerance test 2 h level (glucose concentration of intravenous plasma) of not less than 200 mg/dl.

According to the above-mentioned reports, impaired glucose tolerance is a condition showing a fasting blood glucose level (glucose concentration of intravenous plasma) of less than 126 mg/dl and a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a 75 g oral glucose tolerance test 2 h level (glucose concentration of intravenous plasma) of less than 140 mg/dl is called IFG (Impaired Fasting Glycemia).

The compound (I) can be also used as an agent for improving or an agent for the prophylaxis or treatment of diabetes, borderline type, impaired glucose tolerance abnormality, IFG (Impaired Fasting Glucose) and IFG (Impaired Fasting Glycemia), as determined according to the above-mentioned diagnostic criteria, and further as a therapeutic agent for hypertension of patients with hypertension of the level not less than the above-mentioned diagnostic criteria (e.g., fasting blood sugar level of 126 mg/dl). Moreover, the compound (I) can prevent progress of borderline type, impaired glucose tolerance, IFG (Impaired Fasting Glucose) or IFG (Impaired Fasting Glycemia) into diabetes.

The compound (I) is useful as an agent for the prophylaxis or treatment of metabolic syndrome. Because patients with metabolic syndrome have an extreme high incidence of cardiovascular diseases as compared to patients with single lifestyle-related disease, the prophylaxis or treatment of metabolic syndrome is quite important to prevent cardiovascular diseases.

Criteria for diagnosis of metabolic syndrome are announced by WHO in 1999, and by NCEP in 2001. According to the criterion of WHO, patients with at least two of abdominal obesity, dyslipidemia (high TG or low HDL) and hypertension in addition to hyperinsulinemia or impaired glucose tolerance are diagnosed as metabolic syndrome (World Health Organization: Definition, Diagnosis and Classification of Diabetes Mellitus and Its Complications. Part I: Diagnosis and Classification of Diabetes Mellitus, World Health Organization, Geneva, 1999). According to the criterion of Adult Treatment Panel III of National Cholesterol Education Program, that is an indicator for managing ischemic heart diseases in America, patients with at least three of abdominal obesity, high triglycerides, low HDL cholesterol, hypertension and impaired glucose tolerance are diagnosed as metabolic syndrome (National Cholesterol Education Program: Executive Summary of the Third Report of National Cholesterol Education Program (NCEP) Expert Panel on Detection, Evaluation, and Treatment of High Blood Cholesterol in Adults (Adults Treatment Panel III). The Journal of the American Medical Association, Vol. 285, 2486-2497, 2001).

The compound (I) can be used for treating patients of high blood pressure with metabolic syndrome.

Since compound (I) has an anti-inflammatory action, it can be used as an anti-inflammatory agent for preventing or treating inflammatory diseases. Examples of inflammatory diseases include inflammatory diseases due to various diseases such as arthritis (e.g., chronic rheumatoid arthritis, osteoarthritis, rheumatoid myelitis, gouty arthritis, synovitis), asthma, allergic diseases, arteriosclerosis including atherosclerosis (aneurysm, coronary atherosclerosis, cerebral arterial sclerosis, peripheral arterial sclerosis etc.), digestive tract diseases such as inflammatory bowel diseases (e.g., Crohn's disease, ulcerative colitis), diabetic complications (diabetic nerves disorder, diabetic vascular disorder), atopic dermatitis, chronic obstructive pulmonary disease, systemic lupus erythematosus, visceral inflammatory diseases (nephritis, hepatitis), autoimmune hemolytic anemia, psoriasis, nervous degenerative diseases (e.g., Alzheimer's disease, Parkinson's diseases, amyotrophic lateral sclerosis, AIDS encephalopathy), central nervous disorders (e.g., cerebrovascular disorder such as cerebral hemorrhage and cerebral infarction, head trauma, spinal damage, cerebral edema, multiple sclerosis), meningitis, angina, cardiac infarction, congestive cardiac failure, vascular hypertrophy or occlusion and organ disorders after intervention (percutaneous coronary angioplasty, stenting, coronary angioscopy, intravascular ultrasound, intracoronary thrombolysis etc.), vascular reocclusion and restenosis after bypass surgery, endothelial function disorder, other circulatory diseases (intermittent claudication, obstructive peripheral circulatory diturbance, arteriosclerosis oblit-erans, thromboangiitis obliterans, ischemic cerebral circulatory disorder, Raynaud's disease, Berger disease), inflammatory ocular disease, pulmonary sarcoidosis (e.g., chronic pneumonia, pulmonary silicosis, pulmonary sarcoidosis, pulmonary tuberculosis), endometritis, toxemia (e.g., sepsis, septic shock, endotoxin shock, gram negative sepsis, toxic shock syndrome), cachexia (e.g., cachexia due to infection, carcinomatous cachexia, cachexia due to acquired immunodeficiency syndrome), cancer, Addison's disease, Creutzfeldt-Jakob disease, virus infection (e.g., infection of virus such as cytomegalovirus, influenza virus, herpes virus etc.), disseminated intravascular coagulation and the like. Since compound (I) has an analgesis action, it can also be used as an analgesic agent for preventing or treating pain. Examples of pain diseases include acute pain due to inflammation, pain associated with chronic inflammation, pain associated with acute inflammation, pain after operation (pain of incisional, deep pain, organ pain, chronic pain after operation etc.), muscular pain (muscular pain associated with chronic pain disease, shoulder stiffness etc.), arthralgia, toothache, gnathicarthralgia, headache (migraine, catatonic headache, headache associated with fever, headache associated hypertension), organ pain (cardiac pain, angina pain, abdominal pain, renal pain, ureterane pain, bladder pain), pain in obstetrics area (mittelschmerz, dysmenorrheal, labor pain), neuralgia (disc hernia, nerve root pain, neuralgia after herpes zoster, trigeminal neuralgia), carcinomatous pain, reflex sympathetic atrophy, complex local pain syndrome, and the like. The compound (I) is effective for alleviating various pains such as nervous pain, carcinomatous pain and inflammatory pain directly and rapidly, and exhibits a particularly superior analgesic effect for patients and pathologies (e.g., hypertension, diabetes, etc. and their complications and the like) in which a pain sense threshold has been lowered. Compound (I) is particularly useful as an analgesic agent for pain associated with chronic inflammation or headache associated with hypertension, or a prophylactic or therapeutic drug for inflammatory diseases or pain caused by (1) arteriosclerosis including atherosclerosis, (2) vascular hypertrophy, vascular occlusion and organ disorders after intervention, (3) vascular reocclusion and restenosis after bypass surgery, endothelial function disorder (4) intermittent claudication, (5) obstructive peripheral circulatory disturbance or (6) arteriosclerosis obliterans.

When compound (I) is combined with a calcium antagonist, the solid preparation of the present invention is useful as a drug for the prophylaxis or treatment of the above-mentioned diseases (preferably, a prophylactic or therapeutic drug for hypertension, cardiac failure, diabetic nephropathy or arteriosclerosis, more preferably, a prophylactic or therapeutic drug for hypertension), enables to reduce the doses of compound (I) and a calcium antagonist when used alone, and suppresses side effects.

The compound (I) can be used in combination with one or more different kinds of medicaments (hereinafter sometimes to be abbreviated as "concomitant drug").

In a specific example, compound (I) can be used in combination with one or more kinds of drugs (concomitant drug) selected from therapeutic agents for diabetes, therapeutic agents for diabetic complications, therapeutic agents for hyperlipidemia, antihypertensive agents, antiobestic agents, diuretics, antithrombotic agents and the like.

Here, as the therapeutic agent for diabetes, for example, insulin preparations (e.g., animal insulin preparations extracted from the pancreas of bovine or swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably, hydrochloride), rosiglitazone or a salt thereof (preferably, maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, compounds described in WO2007/013694, WO2007/018314, WO2008/093639 or WO2008/099794), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues (e.g., sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof), dipeptidyl peptidase IV inhibitors (e.g., Alogliptin or a salt thereof (preferably, benzoate), Vildagliptin, Sitagliptin, Saxagliptin, BI1356, GRC8200, MP-513, PF-00734200, PHX1149, SK-0403, ALS2-0426, TA-6666, TS-021, KRP-104, 2-{[6-[(3R)-3-amino-1-piperidinyl]-3,4-dihydro-3-methyl-2,4-dioxo-1(2H)-pyrimidinyl]methyl}-4-fluorobenzonitrile or a salt thereof), β3 agonists (e.g., N-5984), GPR40 agonists (e.g., compounds described in WO2004/041266, WO2004/106276, WO2005/063729, WO2005/063725, WO2005/087710, WO2005/095338, WO2007/013689 or WO2008/001931), GLP-1 receptor agonists (e.g., GLP-1, GLP-1MR agent, Liraglutide, Exenatide, AVE-0010, BIM-51077, Aib(8,35)hGLP-1(7,37)NH2, CJC-1131, Albiglutide), amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists, FBPase inhibitors), SGLT2 (sodium-glucose cotransporter 2) inhibitors (e.g., Depagliflozin, AVE2268, TS-033, YM543, TA-7284, Remogliflozin, ASP1941), SGLT1 inhibitors, 11β-hydroxysteroid dehydrogenase inhibitors (e.g., BVT-3498, INCB-13739), adiponectin or agonist thereof, IKK inhibitors (e.g., AS-2868), leptin resistance improving drugs, somatostatin receptor agonists, glucokinase activators (e.g., Piragliatin, AZD1656, AZD6370, TTP-355, compounds described in WO2006/112549, WO2007/028135, WO2008/047821, WO2008/050821, WO2008/136428 or WO2008/156757), GIP (Glucose-dependent insulinotropic peptide), GPR119 agonists (e.g., PSN821), FGF21, FGF analogue and the like can be mentioned.

As the therapeutic agent for diabetic complications, aldose reductase inhibitors (e.g., tolrestat, epalrestat, zopolrestat, fidarestat, CT-112, ranirestat (AS-3201), lidorestat), neurotrophic factor and increasing agents thereof (e.g., NGF, NT-3, BDNF, neurotrophic production/secretion promoting agent described in WO01/14372 (e.g., 4-(4-chlorophenyl)-2-(2-methyl-1-imidazolyl)-5-[3-(2-methylphenoxy)propyl] oxazole), compounds described in WO2004/039365), PKC inhibitors (e.g., ruboxistaurin mesylate), AGE inhibitors (e.g., ALT946, N-phenacylthiazolium bromide (ALT766), EXO-226, Pyridorin, pyridoxamine), GABA receptor agonists (e.g., gabapentin, pregabalin), serotonin and norepinephrine reuptake inhibitors (e.g., duloxetine), sodium channel inhibitors (e.g., lacosamide), active oxygen scavengers (e.g., thioctic acid), cerebral vasodilators (e.g., tiapuride, mexiletine), somatostatin receptor agonists (e.g., BIM23190), apoptosis signal regulating kinase-1 (ASK-1) inhibitors and the like can be mentioned.

As the therapeutic agent for hyperlipidemia, HMG-CoA reductase inhibitors (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., compounds described in WO97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidin-4-acetic acid), fibrate compounds (e.g., bezafibrate, clofibrate, simfibrate, clinofibrate), anion exchange resin (e.g., colestyramine), probucol, nicotinic acid drugs (e.g., nicomol, niceritrol, niaspan), ethyl icosapentate, phytosterol (e.g., soysterol, gamma oryzanol (γ-oryzanol)), cholesterol absorption inhibitors (e.g., zechia), CETP inhibitors (e.g., dalcetrapib, anacetrapib), ω-3 fatty acid preparations (e.g., ω-3-acid ethyl esters 90) and the like can be mentioned.

As the antihypertensive agent, angiotensin converting enzyme inhibitors (e.g., captopril, enalapril, delapril and the like), angiotensin II antagonists (e.g., candesartan cilexetil, candesartan, losartan, losartan potassium, eprosartan, valsartan, telmisartan, irbesartan, tasosartan, olmesart, olmesartan medoxomil, azilsartan and the like), a calcium antagonists (e.g., manidipine, nifedipine, amlodipine, efonidipine, nicardipine, amlodipine, cilnidipine and the like), β blockers (e.g., metoprolol, atenolol, propranolol, carvedilol, pindolol and the like), clonidine and the like can be mentioned.

As the antiobesity agent, monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptor, GABA-regulating drugs (e.g., topiramate), neuropeptide Y antagonists (e.g., velneperit), cannabinoid receptor antagonists (e.g., rimonabant, taranabant), ghrelinant agonists, ghrelin receptor antagonists, ghrelin acylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), β3 agonists (e.g., N-5984), diacylglycerol acyltransferase 1 (DGAT1) inhibitors, acetyl CoA carboxylase (ACC) inhibitors, steaoryl-CoA desaturase inhibitors, microsomal triglyceride transfer protein inhibitors (e.g., R-256918), Na-glucose cotransporter inhibitors (e.g., JNJ-28431754, remogliflozin), NFκB inhibitors (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN-821), glucokinase activators (e.g., AZD-1656), leptin, leptin derivatives (e.g., meterleptin), CNTF (ciliary neurotrophic factor), BDNF (brain-derived neurotrophic factor), cholecystokinin agonists, glucagon-like peptide-1 (GLP-1) preparations (e.g., animal GLP-1 preparations extracted from the pancreas of bovine or swine; human GLP-1 preparations genetically synthesized using *Escherichia coli* or yeast; fragment or derivative of GLP-1 (e.g., exenatide, liraglutide)), amylin preparations (e.g., pramlintide, AC-2307), neuropeptide Y agonists (e.g., PYY3-36, derivative of PYY3-36, obinepitide, TM-30339, TM-30335), oxyntomodulin preparations; FGF21 preparations (e.g., animal FGF21 preparations extracted from the pancreas of bovine or swine; human FGF21 preparations genetically synthesized using *Escherichia coli* or yeast; fragment or derivative of FGF21)), feeding deterrents (e.g., P-57) and the like can be mentioned.

As the diuretic, for example, xanthine derivatives (e.g., theobromine sodium salicylate, theobromine calcium salicylate and the like), thiazide preparations (e.g., ethiazide, cyclopenthiazide, trichloromethyazide, hydrochlorothiazide, hydroflumethiazide, benzylhydrochlorothiazide, penfluthiazide, poly 5 thiazide, methyclothiazide and the like), antialdosterone preparations (e.g., spironolactone, triamterene and the like), carbonic anhydrase inhibitors (e.g., acetazolamide and the like), chlorobenzenesulfonamide agents (e.g., chlortalidone, mefruside, indapamide and the like), azosemide, isosorbide, ethacrynic acid, piretanide, bumetanide, furosemide and the like can be mentioned.

As the antithrombotic agents, for example, heparin (e.g., heparin sodium, heparin calcium, enoxaparin sodium, dalteparin sodium), warfarin (e.g., warfarin potassium), antithrombin drugs (e.g., aragatroban, dabigatran), FXa inhibitors (e.g., rivaroxaban, apixaban, edoxaban, YM150, compounds described in WO02/06234, WO2004/048363, WO2005/030740, WO2005/058823 or WO2005/113504), thrombolytic agents (e.g., urokinase, tisokinase, alteplase, nateplase, monteplase, pamiteplase), platelet aggregation inhibitors (e.g., ticlopidine hydrochloride, clopidogrel, prasugrel, E5555, SHC530348, cilostazol, ethyl icosapentate, beraprost sodium, sarpogrelate hydrochloride) and the like can be mentioned.

When the solid preparation of the present invention and a concomitant drug are used in combination, the administration period thereof is not limited, and they may be administered simultaneously or in a staggered manner to the administration subject.

Moreover, the solid preparation of the present invention and a concomitant drug may be administered as separate preparations, or as a single preparation containing the solid preparation of the present invention and a concomitant drug.

The dose of the concomitant drug can be appropriately determined based on the dose employed in clinical situations of each drug. The mixing ratio of the solid preparation of the present invention and a concomitant drug can be appropriately determined depending on the administration subject, administration route, target disease, symptom, combination and the like. When the subject of administration is human, for example, a concomitant drug can be used in 0.01 to 100 parts by weight relative to 1 part by weight of the solid preparation of the present invention.

Using a concomitant drug in this way, superior effects of
1) an effect of enhancing the action of compound (I) or a concomitant drug (synergistic effect of medicament actions);
2) an effect of reducing the dose of compound (I) or a concomitant drug (medicament dose-reducing effect as compared to single administration);
3) an effect of reducing the secondary action of compound (I) or a concomitant drug;
and the like can be obtained.

The present invention provides a method of stabilizing a compound represented by the formula (I) or a salt thereof and a calcium antagonist in a solid preparation comprising the compound represented by the formula (I) or a salt thereof, and a calcium antagonist, which method comprising adding a pH control agent. According to the stabilizing method of the present invention, compound (I) in the solid preparation can be significantly stabilized. In addition, the present invention also provides a method of improving dissolution of a compound represented by the formula (I) or a salt thereof from a solid preparation comprising the compound represented by the formula (I) or a salt thereof, and a calcium antagonist, which method comprising adding a pH control agent. According to the improvement method of dissolution property in the present invention, the dissolution property of compound (I) from a solid preparation can be significantly improved.

The present invention is explained in more detail in the following by referring to Preparation Examples, Reference Examples, Comparative Examples and Experimental Examples, which are not to be construed as limitative.

As the ingredients (additives) other than the active ingredient in the pharmaceutical preparations described in the Preparation Examples, Reference Examples and Comparative Examples, compatible products of the Japanese. Pharmacopoeia, the Japanese Pharmaceutical Codex or Japanese Pharmaceutical Excipients were used.

EXAMPLES

Formulation Example 1

(1) Hydroxypropylcellulose (5124 g) was dissolved in purified water (80280 g) to give binder liquid I. Amlodipine besylate (2984 g), mannitol (55840 g) and crystalline cellulose (3870 g) were uniformly mixed in a fluid bed granulator (WSG-60, POWREX CORPORATION), and granulated by spraying the binder liquid I (38700 g) and then dried to give granules. A part of the obtained granules was milled in a powermill grinder (P-7S, Showa Chemical Machinery) using 1.5 mmφ punching screen to give milled granules. Crystalline cellulose (7200 g), crospovidone (3600 g), magnesium stearate (720 g) and the milled granules (60480 g) were mixed in a tumbler mixer (TM-400S, Showa Chemical Machinery) to give mixed granules A.

(2) Sodium hydroxide (405.8 g) and fumaric acid (1176 g) were dissolved in purified water (38230 g) to give a buffer solution. Hydroxypropylcellulose (3018 g) was dissolved in purified water (47280 g) to give binder liquid II. Compound A (20060 g), mannitol (40860 g), crystalline cellulose (4230 g) were uniformly mixed in a fluid bed granulator (WSG-60, POWREX CORPORATION), and granulated by spraying the buffer solution (31810 g) and further the binder liquid II (42300 g), and dried to give granules. A part of the obtained granules were milled in a powermill grinder (P-7S, Showa Chemical Machinery) using 1.5 mmφ punching screen to give milled granules. Crystalline cellulose (7380 g), crospovidone (5535 g), magnesium stearate (738 g) and the milled granules (60150 g) were mixed in a tumbler mixer (TM-400S, Showa Chemical Machinery) to give mixed granules B.

(3) The mixed granules A (180 mg) and the mixed granules B (90 mg) were tableted in the form of bi-layer by a rotary tableting machine (AQUA 08242L2JI, Kikusui Seisakusho, Ltd.) with 8.5 mmφ punch (tableting pressure 8 KN, weight per tablet: 270 mg) to give plain tablets.

(4) Hydroxypropylmethylcellulose (468 g) and talc (72 g) were dissolved and dispersed in purified water (4320 g) to give dispersion liquid I. Titanium oxide (54 g) and iron oxide (6 g) were dispersed in purified water (900 g) to give dispersion liquid II. The dispersion liquid I was mixed with the dispersion liquid II and purified water (180 g) to give a coating dispersion. Using a pan coating machine (DRC-650, POWREX CORPORATION), the coating dispersion was sprayed until the weight of the plain tablets obtained in (3) increased by 10 mg per tablet, whereby film-coated tablets having the following composition were obtained. Then, the film-coated tablets were dried under the reduced pressure at 40° C. for 18 hr.

| composition of preparation (per 280 mg) | |
|---|---:|
| amlodipine besylate | 6.94 mg |
| mannitol | 129.86 mg |
| crystalline cellulose | 9 mg |
| hydroxypropylcellulose | 5.4 mg |
| crystalline cellulose | 18 mg |

-continued

| composition of preparation (per 280 mg) | |
|---|---|
| crospovidone | 9 mg |
| magnesium stearate | 1.8 mg |
| compound A | 21.34 mg |
| mannitol | 43.465 mg |
| crystalline cellulose | 4.5 mg |
| sodium hydroxide | 0.345 mg |
| fumaric acid | 1 mg |
| hydroxypropylcellulose | 2.7 mg |
| crystalline cellulose | 9 mg |
| crospovidone | 6.75 mg |
| magnesium stearate | 0.9 mg |
| hydroxypropylmethylcellulose | 7.8 mg |
| talc | 1.2 mg |
| titanium oxide | 0.9 mg |
| iron oxide | 0.1 mg |
| total | 280 mg |

Formulation Example 2

(1) Hydroxypropylcellulose (5124 g) was dissolved in purified water (80280 g) to give binder liquid I. Amlodipine besylate (5964 g), mannitol (52860 g) and crystalline cellulose (3870 g) were uniformly mixed in a fluid bed granulator (WSG-60, POWREX CORPORATION), and granulated by spraying the binder liquid I (38700 g) and then dried to give granules. A part of the obtained granules was milled in a powermill grinder (P-7S, Showa Chemical Machinery) using 1.5 mmϕ punching screen to give milled granules. Crystalline cellulose (7200 g), crospovidone (3600 g), magnesium stearate (720 g) and the milled granules (60480 g) were mixed in a tumbler mixer (TM-400S, Showa Chemical Machinery) to give mixed granules A.

(2) Sodium hydroxide (405.8 g) and fumaric acid (1176 g) were dissolved in purified water (38230 g) to give a buffer solution. Hydroxypropylcellulose (3018 g) was dissolved in purified water (47280 g) to give binder liquid II. Compound A (20060 g), mannitol (40860 g) and crystalline cellulose (4230 g) were uniformly mixed in a fluid bed granulator (WSG-60, POWREX CORPORATION) and granulated by spraying the buffer solution (31810 g) and then the binder liquid II (42300 g), and then dried to give granules. A part of the obtained granules was milled in a powermill grinder (P-7S, Showa Chemical Machinery) using 1.5 mmϕ punching screen to give milled granules. Crystalline cellulose (7380 g), crospovidone (5535 g), magnesium stearate (738 g) and the milled granules (58680 g) were mixed in a tumbler mixer (TM-400S, Showa Chemical Machinery) to give mixed granules B.

(3) The mixed granules A (180 mg) and the mixed granules B (90 mg) were tableted in the form of a bi-layer by a rotary tableting machine (AQUA 08242L2JI, Kikusui Seisakusho, Ltd.) with 8.5 mmϕ punch (tableting pressure 8 KN, weight per tablet: 270 mg) to give plain tablets.

(4) Hydroxypropylmethylcellulose (468 g) and talc (72 g) were dissolved and dispersed in purified water (4320 g) to give dispersion liquid I. Titanium oxide (54 g) and iron oxide (6 g) were dispersed in purified water (900 g) to give dispersion liquid II. The dispersion liquid I was mixed with the dispersion liquid II and purified water (180 g) to give a coating dispersion. Using a pan coating machine (DRC-650, POWREX CORPORATION), the coating dispersion was sprayed until the weight of the plain tablets obtained in (3) increased by 10 mg per tablet, whereby film-coated tablets having the following composition were obtained. Then, the film-coated tablets were dried under the reduced pressure at 40° C. for 18 hr.

| composition of preparation (per 280 mg) | |
|---|---|
| amlodipine besylate | 13.87 mg |
| mannitol | 122.93 mg |
| crystalline cellulose | 9 mg |
| hydroxypropylcellulose | 5.4 mg |
| crystalline cellulose | 18 mg |
| crospovidone | 9 mg |
| magnesium stearate | 1.8 mg |
| compound A | 21.34 mg |
| mannitol | 43.465 mg |
| crystalline cellulose | 4.5 mg |
| sodium hydroxide | 0.345 mg |
| fumaric acid | 1 mg |
| hydroxypropylcellulose | 2.7 mg |
| crystalline cellulose | 9 mg |
| crospovidone | 6.75 mg |
| magnesium stearate | 0.9 mg |
| hydroxypropylmethylcellulose | 7.8 mg |
| talc | 1.2 mg |
| titanium oxide | 0.9 mg |
| iron oxide | 0.1 mg |
| total | 280 mg |

Formulation Example 3

(1) Hydroxypropylcellulose (5124 g) was dissolved in purified water (80280 g) to give binder liquid I. Amlodipine besylate (2984 g), mannitol (55840 g) and crystalline cellulose (3870 g) were uniformly mixed in a fluid bed granulator (WSG-60, POWREX CORPORATION), and granulated by spraying the binder liquid I (38700 g) and then dried to give granules. A part of the obtained granules was milled in a powermill grinder (P-7S, Showa Chemical Machinery) with 1.5 mmϕ punching screen to give milled granules. Crystalline cellulose (7200 g), crospovidone (3600 g), magnesium stearate (720 g) and the milled granules (60480 g) were mixed in a tumbler mixer (TM-400S, Showa Chemical Machinery) to give mixed granules A.

(2) Sodium hydroxide (405.8 g) and fumaric acid (1176 g) were dissolved in purified water (38230 g) to give a buffer solution. Hydroxypropylcellulose (3018 g) was dissolved in purified water (47280 g) to give binder liquid II. Compound A (20060 g), mannitol (40860 g) and crystalline cellulose (4230 g) were uniformly mixed in a fluid bed granulator (WSG-60, POWREX CORPORATION), and granulated by spraying the buffer solution (31810 g) and then the binder liquid II (42300 g), and then dried to give granules. A part of the obtained granules was milled in a powermill grinder (P-7S, Showa Chemical Machinery) with 1.5 mmϕ punching screen to give milled granules. Crystalline cellulose (7380 g), crospovidone (5535 g), magnesium stearate (738 g) and the milled granules (60150 g) were mixed in a tumbler mixer (TM-400S, Showa Chemical Machinery) to give mixed granules B.

(3) The mixed granules A (180 mg) and the mixed granules B (360 mg) were tableted in the form of bi-layer by a rotary tableting machine (AQUA 08242L2JI, Kikusui Seisakusho, Ltd.) with a punch having a major axis 14 mm, a miner axis 8 mm (tableting pressure 9 KN, weight per tablet: 540 mg) to give plain tablets.

(4) Hydroxypropylmethylcellulose (468 g) and talc (72 g) were dissolved and dispersed in purified water (4320 g) to give dispersion liquid I. Titanium oxide (54 g) and iron oxide (6 g) were dispersed in purified water (900 g) to give dispersion liquid II. The dispersion liquid I was mixed with the dispersion liquid II and purified water (180 g) to give a coating dispersion. Using a pan coating machine (DRC-650, POWREX CORPORATION), the coating dispersion was sprayed until the weight of the plain tablets obtained in (3) increased by 20 mg per tablet, whereby film-coated tablets having the following composition were obtained. Then, the film-coated tablets were dried under the reduced pressure at 40° C. for 18 hr.

| composition of preparation (per 560 mg) | |
| --- | --- |
| amlodipine besylate | 6.94 mg |
| mannitol | 129.86 mg |
| crystalline cellulose | 9 mg |
| hydroxypropylcellulose | 5.4 mg |
| crystalline cellulose | 18 mg |
| crospovidone | 9 mg |
| magnesium stearate | 1.8 mg |
| compound A | 85.36 mg |
| mannitol | 173.86 mg |
| crystalline cellulose | 18 mg |
| sodium hydroxide | 1.38 mg |
| fumaric acid | 4 mg |
| hydroxypropylcellulose | 10.8 mg |
| crystalline cellulose | 36 mg |
| crospovidone | 27 mg |
| magnesium stearate | 3.6 mg |
| hydroxypropylmethylcellulose | 15.6 mg |
| talc | 2.4 mg |
| titanium oxide | 1.8 mg |
| iron oxide | 0.2 mg |
| total | 560 mg |

Formulation Example 4

(1) Hydroxypropylcellulose (5124 g) was dissolved in purified water (80280 g) to give binder liquid I. Amlodipine besylate (5964 g), mannitol (52860 g) and crystalline cellulose (3870 g) were uniformly mixed in a fluid bed granulator (WSG-60, POWREX CORPORATION), and granulated by spraying the binder liquid I (38700 g) and then dried to give granules. A part of the obtained granules was milled in a powermill grinder (P-7S, Showa Chemical Machinery) with 1.5 mmφ punching screen to give milled granules. Crystalline cellulose (7200 g), crospovidone (3600 g), magnesium stearate (720 g) and the milled granules (60480 g) were mixed in a tumbler mixer (TM-400S, Showa Chemical Machinery) to give mixed granules A.

(2) Sodium hydroxide (405.8 g) and fumaric acid (1176 g) were dissolved in purified water (38230 g) to give a buffer solution. Hydroxypropylcellulose (3018 g) was dissolved in purified water (47280 g) to give binder liquid II. Compound A (20060 g), mannitol (40860 g) and crystalline cellulose (4230 g) were uniformly mixed in a fluid bed granulator (WSG-60, POWREX CORPORATION), and granulated by spraying the buffer solution (31810 g) and then the binder liquid II (42300 g), and then dried to give granules. A part of the obtained granules was milled in a powermill grinder (P-7S, Showa Chemical Machinery) with 1.5 mmφ punching screen to give milled granules. Crystalline cellulose (7380 g), crospovidone (5535 g), magnesium stearate (738 g) and the milled granules (60150 g) were mixed in a tumbler mixer (TM-400S, Showa Chemical Machinery) to give mixed granules B.

(3) The mixed granules A (180 mg) and the mixed granules B (360 mg) were tableted in the form of a bi-layer by a rotary tableting machine (AQUA 08242L2JI, Kikusui Seisakusho, Ltd.) with a punch having a major axis 14 mm, a miner axis 8 mm (tableting pressure 9 kN, weight per tablet: 540 mg) to give plain tablets.

(4) Hydroxypropylmethylcellulose (468 g) and talc (72 g) were dissolved and dispersed in purified water (4320 g) to give dispersion liquid I. Titanium oxide (54 g) and iron oxide (6 g) were dispersed in purified water (900 g) to give dispersion liquid II. The dispersion liquid I was mixed with the dispersion liquid II and purified water (180 g) to give a coating dispersion. Using a pan coating machine (DRC-650, POWREX CORPORATION), the coating dispersion was sprayed until the weight of the plain tablets obtained in (3) increased by 20 mg per tablet, whereby film-coated tablets having the following composition were obtained. Then, the film-coated tablets were dried under the reduced pressure at 40° C. for 18 hr.

| composition of preparation (per 560 mg) | |
| --- | --- |
| amlodipine besylate | 13.87 mg |
| mannitol | 122.93 mg |
| crystalline cellulose | 9 mg |
| hydroxypropylcellulose | 5.4 mg |
| crystalline cellulose | 18 mg |
| crospovidone | 9 mg |
| magnesium stearate | 1.8 mg |
| compound A | 85.36 mg |
| mannitol | 173.86 mg |
| crystalline cellulose | 18 mg |
| sodium hydroxide | 1.38 mg |
| fumaric acid | 4 mg |
| hydroxypropylcellulose | 10.8 mg |
| crystalline cellulose | 36 mg |
| crospovidone | 27 mg |
| magnesium stearate | 3.6 mg |
| hydroxypropylmethylcellulose | 15.6 mg |
| talc | 2.4 mg |
| titanium oxide | 1.8 mg |
| iron oxide | 0.2 mg |
| total | 560 mg |

Formulation Example 5

(1) Hydroxypropylcellulose (5124 g) was dissolved in purified water (80280 g) to give binder liquid I. Amlodipine besylate (2984 g), mannitol (55840 g) and crystalline cellulose (3870 g) were uniformly mixed in a fluid bed granulator (WSG-60, POWREX CORPORATION), and granulated by spraying the binder liquid I (38700 g) and then dried to give granules. A part of the obtained granules was milled in a powermill grinder (P-7S, Showa Chemical Machinery) with 1.5 mmφ punching screen to give is milled granules A.

(2) Sodium hydroxide (405.8 g) and fumaric acid (1176 g) were dissolved in purified water (38230 g) to give a buffer solution. Hydroxypropylcellulose (3018 g) was dissolved in purified water (47280 g) to give binder liquid II. Compound A (20060 g), mannitol (40860 g) and crystalline cellulose (4230 g) were uniformly mixed in a fluid bed granulator (WSG-60, POWREX CORPORATION) and granulated by spraying the buffer solution (31810 g) and then the binder liquid II (42300 g), and then dried to give granules. A part of the obtained granules was milled in a powermill grinder (P-7S, Showa Chemical Machinery) with 1.5 mmφ punching screen to give milled granules B.

(3) Crystalline cellulose (1620 g), crospovidone (945 g), magnesium stearate (162 g), the milled granules A (9072 g)

and milled granules B (4401 g) were mixed in a tumbler mixer (TM-100, Showa Chemical Machinery) to give mixed granules.
(4) The mixed granules were tableted by a rotary tableting machine (AQUA 512SS2AI, Kikusui Seisakusho, Ltd.) with 8.5 mmφ punch (tableting pressure: 7 KN, weight per tablet: 270 mg) to give plain tablets.
(5) Hydroxypropylmethylcellulose (468 g) and talc (72 g) were dissolved and dispersed in purified water (4320 g) to give dispersion liquid I. Titanium oxide (54 g) and iron oxide (6 g) were dispersed in purified water (900 g) to give dispersion liquid II. The dispersion liquid I was mixed with the dispersion liquid II and purified water (180 g) to give a coating dispersion. Using a pan coating machine (DRC-650, POWREX CORPORATION), the coating dispersion was sprayed until the weight of the plain tablets obtained in (4) increased by 10 mg per tablet, whereby film-coated tablets having the following composition were obtained. Then, the film-coated tablets were dried under reduced the pressure at 40° C. for 18 hr.

| composition of preparation (per 280 mg) | |
| --- | --- |
| amlodipine besylate | 6.94 mg |
| mannitol | 129.86 mg |
| crystalline cellulose | 9 mg |
| hydroxypropylcellulose | 5.4 mg |
| compound A | 21.34 mg |
| mannitol | 43.465 mg |
| crystalline cellulose | 4.5 mg |
| sodium hydroxide | 0.345 mg |
| fumaric acid | 1 mg |
| hydroxypropylcellulose | 2.7 mg |
| crystalline cellulose | 27 mg |
| crospovidone | 15.75 mg |
| magnesium stearate | 2.7 mg |
| hydroxypropylmethylcellulose | 7.8 mg |
| talc | 1.2 mg |
| titanium oxide | 0.9 mg |
| iron oxide | 0.1 mg |
| total | 280 mg |

Formulation Example 6

(1) Hydroxypropylcellulose (5124 g) was dissolved in purified water (80280 g) to give binder liquid I. Amlodipine besylate (5964 g), mannitol (52860 g) and crystalline cellulose (3870 g) were uniformly mixed in a fluid bed granulator (WSG-60, POWREX CORPORATION), and granulated by spraying the binder liquid I (38700 g) and then dried to give granules. A part of the obtained granules was milled in a powermill grinder (P-7S, Showa Chemical Machinery) with 1.5 mmφ punching screen to give milled granules A.
(2) Sodium hydroxide (405.8 g) and fumaric acid (1176 g) were dissolved in purified water (38230 g) to give a buffer solution. Hydroxypropylcellulose (3018 g) was dissolved in purified water (47280 g) to give binder liquid II. Compound A (20060 g), mannitol (40860 g) and crystalline cellulose (4230 g) were uniformly mixed in a fluid bed granulator (WSG-60, POWREX CORPORATION) and granulated by spraying the buffer solution (31810 g) and then the binder liquid II (42300 g), and then dried to give granules. A part of the obtained granules was milled in a powermill grinder (P-7S, Showa Chemical Machinery) with 1.5 mmφ punching screen to give milled granules B.

(3) Crystalline cellulose (1620 g), crospovidone (945 g), magnesium stearate (162 g), the milled granules A (9072 g) and milled granules B (4401 g) were mixed in a tumbler mixer (TM-60S, Showa Chemical Machinery) to give mixed granules.
(4) The mixed granules were tableted by a rotary tableting machine (AQUA 512SS2AI, Kikusui Seisakusho, Ltd.) with 8.5 mm4 punch (tableting pressure: 7 KN, weight per tablet: 270 mg) to give plain tablets.
(5) Hydroxypropylmethylcellulose (468 g) and talc (72 g) were dissolved and dispersed in purified water (4320 g) to give dispersion liquid I. Titanium oxide (54 g) and iron oxide (6 g) were dispersed in purified water (900 g) to give dispersion liquid II. The dispersion liquid I was mixed with the dispersion liquid II and purified water (180 g) to give a coating dispersion. Using a pan coating machine (DRC-650, POWREX CORPORATION), the coating dispersion was sprayed until the weight of the plain tablets obtained in (4) increased by 10 mg per tablet, whereby film-coated tablets having the following composition were obtained. Then, the film-coated tablets were dried under the reduced pressure at 40° C. for 18 hr.

| composition of preparation (per 280 mg) | |
| --- | --- |
| amlodipine besylate | 13.87 mg |
| mannitol | 122.93 mg |
| crystalline cellulose | 9 mg |
| hydroxypropylcellulose | 5.4 mg |
| compound A | 21.34 mg |
| mannitol | 43.465 mg |
| crystalline cellulose | 4.5 mg |
| sodium hydroxide | 0.345 mg |
| fumaric acid | 1 mg |
| hydroxypropylcellulose | 2.7 mg |
| crystalline cellulose | 27 mg |
| crospovidone | 15.75 mg |
| magnesium stearate | 2.7 mg |
| hydroxypropylmethylcellulose | 7.8 mg |
| talc | 1.2 mg |
| titanium oxide | 0.9 mg |
| iron oxide | 0.1 mg |
| total | 280 mg |

Formulation Example 7

(1) Hydroxypropylcellulose (5124 g) was dissolved in purified water (80280 g) to give binder liquid I. Amlodipine besylate (2984 g), mannitol (55840 g) and crystalline cellulose (3870 g) were uniformly mixed in a fluid bed granulator (WSG-60, POWREX CORPORATION), and granulated by spraying the binder liquid I (38700 g) and then dried to give granules. A part of the obtained granules was milled in a powermill grinder (P-7S, Showa Chemical Machinery) with 1.5 mmφ punching screen to give milled granules A.
(2) Sodium hydroxide (405.8 g) and fumaric acid (1176 g) were dissolved in purified water (38230 g) to give a buffer solution. Hydroxypropylcellulose (3018 g) was dissolved in purified water (47280 g) to give binder liquid II. Compound A (20060 g), mannitol (40860 g) and crystalline cellulose (4230 g) were uniformly mixed in a fluid bed granulator (WSG-60, POWREX CORPORATION) and granulated by spraying the buffer solution (31810 g) and then the binder liquid II (42300 g), and then dried to give granules. A part of the obtained granules was milled in a powermill grinder (P-7S, Showa Chemical Machinery) with 1.5 mmφ punching screen to give milled granules B.
(3) Crystalline cellulose (1620 g), crospovidone (1080 g), magnesium stearate (162 g), the milled granules A (4536 g) and milled granules B (8802 g) were mixed in a tumbler mixer (TM-60S, Showa Chemical Machinery) to give mixed granules.
(4) The mixed granules were tableted by a rotary tableting machine (AQUA 512SS2AI, Kikusui Seisakusho, Ltd.) with a punch having a major axis 14 mm, a miner axis 8 mm (tableting pressure: 9 KN, weight per tablet: 540 mg) to give plain tablets.
(5) Hydroxypropylmethylcellulose (468 g) and talc (72 g) were dissolved and dispersed in purified water (4320 g) to give dispersion liquid I. Titanium oxide (54 g) and iron oxide (6 g) were dispersed in purified water (900 g) to give dispersion liquid II. The dispersion liquid I was mixed with the dispersion liquid II and purified water (180 g) to give a coating dispersion. Using a pan coating machine (DRC-650, POWREX CORPORATION), the coating dispersion was sprayed until the weight of the plain tablets obtained in (4) increased by 20 mg per tablet, whereby film-coated tablets having the following composition were obtained. Then, the film-coated tablets were dried under the reduced pressure at 40° C. for 18 hr.

| composition of preparation (per 560 mg) | |
| --- | --- |
| amlodipine besylate | 6.94 mg |
| mannitol | 129.86 mg |
| crystalline cellulose | 9 mg |
| hydroxypropylcellulose | 5.4 mg |
| compound A | 85.36 mg |
| mannitol | 173.86 mg |
| crystalline cellulose | 18 mg |
| sodium hydroxide | 1.38 mg |
| fumaric acid | 4 mg |
| hydroxypropylcellulose | 10.8 mg |
| crystalline cellulose | 54 mg |
| crospovidone | 36 mg |
| magnesium stearate | 5.4 mg |
| hydroxypropylmethylcellulose | 15.6 mg |
| talc | 2.4 mg |
| titanium oxide | 1.8 mg |
| iron oxide | 0.2 mg |
| total | 560 mg |

Formulation Example 8

(1) Hydroxypropylcellulose (5124 g) was dissolved in purified water (80280 g) to give binder liquid I. Amlodipine besylate (5964 g), mannitol (52860 g) and crystalline cellulose (3870 g) were uniformly mixed in a fluid bed granulator (WSG-60, POWREX CORPORATION), and granulated by spraying the binder liquid I (38700 g) and then dried to give granules. A part of the obtained granules was milled in a powermill grinder (P-7S, Showa Chemical Machinery) with 1.5 mmφ punching screen to give milled granules A.
(2) Sodium hydroxide (405.8 g) and fumaric acid (1176 g) were dissolved in purified water (38230 g) to give a buffer solution. Hydroxypropylcellulose (3018 g) was dissolved in purified water (47280 g) to give binder liquid II. Compound A (20060 g), mannitol (40860 g), crystalline cellulose (4230 g) were uniformly mixed in a fluid bed granulator (WSG-60, POWREX CORPORATION) and granulated by spraying the buffer solution (31810 g) and then the binder liquid II (42300 g), and then dried to give granules. A part of the obtained granules was milled in a powermill grinder (P-7S, Showa Chemical Machinery) with 1.5 mmφ punching screen to give milled granules B.
(3) Crystalline cellulose (1620 g), crospovidone (1080 g), magnesium stearate (162 g), the milled granules A (4536 g) and milled granules B (8802 g) were mixed in a tumbler mixer (TM-60S, Showa Chemical Machinery) to give mixed granules.
(4) The mixed granules were tableted with a rotary tableting machine (AQUA 512SS2AI, Kikusui Seisakusho, Ltd.) with a punch having a major axis 14 mm, a miner axis 8 mm (tableting pressure: 9 KN, weight per tablet: 540 mg) to give plain tablets.
(5) Hydroxypropylmethylcellulose (468 g) and talc (72 g) were dissolved and dispersed in purified water (4320 g) to give dispersion liquid I. Titanium oxide (54 g) and iron oxide (6 g) were dispersed in purified water (900 g) to give dispersion liquid II. The dispersion liquid I was mixed with the dispersion liquid II and purified water (180 g) to give a coating dispersion. Using a pan coating machine (DRC-650, POWREX CORPORATION), the coating dispersion was sprayed until the weight of the plain tablets obtained in (4) increased by 20 mg per tablet, whereby film-coated tablets having the following composition were obtained. Then, the film-coated tablets were dried under the reduced pressure at 40° C. for 18 hr.

| composition of preparation (per 560 mg) | |
| --- | --- |
| amlodipine besylate | 13.87 mg |
| mannitol | 122.93 mg |
| crystalline cellulose | 9 mg |
| hydroxypropylcellulose | 5.4 mg |
| compound A | 85.36 mg |
| mannitol | 173.86 mg |
| crystalline cellulose | 18 mg |
| sodium hydroxide | 1.38 mg |
| fumaric acid | 4 mg |
| hydroxypropylcellulose | 10.8 mg |
| crystalline cellulose | 54 mg |
| crospovidone | 36 mg |
| magnesium stearate | 5.4 mg |
| hydroxypropylmethylcellulose | 15.6 mg |
| talc | 2.4 mg |
| titanium oxide | 1.8 mg |
| iron oxide | 0.2 mg |
| total | 560 mg |

Formulation Example 9

(1) Hydroxypropylcellulose (162 g) was dissolved in purified water (2538 g) to give binder liquid I. Amlodipine besylate (416.9 g), mannitol (3687 g) and crystalline cellulose (270 g) were uniformly mixed in a fluid bed granulator (FD-5S, POWREX CORPORATION), and granulated by spraying the binder liquid I and then dried to give granules. A part of the obtained granules was milled in a powermill grinder (P-3, Showa Chemical Machinery) with 1.5 mmφ punching screen to give milled granules. Crystalline cellulose (396 g), crospovidone (198 g), magnesium stearate (39.6 g) and the milled granules (3326 g) were mixed in a tumbler mixer (TM-60S, Showa Chemical Machinery) to give mixed granules A.
(2) Sodium hydroxide (62.1 g) and fumaric acid (180 g) were dissolved in purified water (5850 g) to give a buffer solution. Hydroxypropylcellulose (486 g) was dissolved in purified water (7614 g) to give binder liquid II. Compound A (1196 g), mannitol (2433 g) and crystalline cellulose (252 g) were uniformly mixed in a fluid bed granulator (FD-5S, POWREX CORPORATION), and granulated by spraying the buffer solution (1895 g) and then the binder liquid II (2520 g), and then dried to give granules. A part of the obtained granules was milled in a powermill grinder (P-3, Showa Chemical Machinery) with 1.5 mmφ punching screen to give milled granules. Crystalline cellulose (792 g), crospovidone (594 g), magnesium stearate (79.2 g) and the milled granules (6455 g) were mixed in a tumbler mixer (TM-60S, Showa Chemical Machinery) to give mixed granules B.

(3) The mixed granules A (180 mg) and the mixed granules B (360 mg) were tableted in the form of a bi-layer with a rotary tableting machine (AQUA 08242L2JI, Kikusui Seisakusho, Ltd.) with a punch having a major axis 14.8 mm, a miner axis 8 mm (tableting pressure 11KN, weight per tablet: 540 mg) to give plain tablets.

(4) Hydroxypropylmethylcellulose (390 g) and talc (60 g) were dissolved and dispersed in purified water (3500 g) to give dispersion liquid I. Titanium oxide (45 g) and iron oxide (5 g) were dispersed in purified water (750 g) to give dispersion liquid II. The dispersion liquid I was mixed with the dispersion liquid II and purified water (250 g) to give a coating suspension. Using a pan coating machine (DRC-500, POWREX CORPORATION), the coating dispersion was sprayed until the weight of the plain tablets obtained in (3) increased by 20 mg per tablet, whereby film-coated tablets having the following composition were obtained. Then, the film-coated tablets were dried under the reduced pressure at 40° C. for 16 hr.

| composition of preparation (per 560 mg) | |
|---|---|
| amlodipine besylate | 13.87 mg |
| mannitol | 122.93 mg |
| crystalline cellulose | 9 mg |
| hydroxypropylcellulose | 5.4 mg |
| crystalline cellulose | 18 mg |
| crospovidone | 9 mg |
| magnesium stearate | 1.8 mg |
| compound A | 85.36 mg |
| mannitol | 173.86 mg |
| crystalline cellulose | 18 mg |
| sodium hydroxide | 1.38 mg |
| fumaric acid | 4 mg |
| hydroxypropylcellulose | 10.8 mg |
| crystalline cellulose | 36 mg |
| crospovidone | 27 mg |
| magnesium stearate | 3.6 mg |
| hydroxypropylmethylcellulose | 15.6 mg |
| talc | 2.4 mg |
| titanium oxide | 1.8 mg |
| iron oxide | 0.2 mg |
| total | 560 mg |

Reference Example 1

Compound A (42.68 g), lactose (217.32 g), crystalline cellulose (32 g) and monosodium fumarate (10 g) were uniformly mixed in a fluid bed granulator (Lab-1, POWREX CORPORATION), and granulated by spraying an aqueous solution of hydroxypropylcellulose (12 g) and monosodium fumarate (10 g), and then dried in the fluid bed granulator. The obtained granules were passed through 16 mesh sieves (aperture 1.0 mm) to give sieved granules. Low-substituted hydroxypropylcellulose (0.8 g) and the sieved granules (16.2 g) were mixed in a glass bottle. The obtained mixed granules were tableted with an Autograph (manufactured by Shimadzu Corporation, AG-5000B) using a 9.5 mm(1) punch (tableting pressure: 7.5 KN/punch, weight per tablet: 398.3 mg) to give plain tablets having the following composition. Then, the plain tablets were dried under the reduced pressure at 40° C. for 16 hr.

| composition of preparation (per 398.3 mg) | |
|---|---|
| compound A | 50 mg |
| lactose | 254.6 mg |
| crystalline cellulose | 37.5 mg |
| hydroxypropylcellulose | 14.1 mg |
| monosodium fumarate | 23.4 mg |
| low-substituted hydroxypropylcellulose | 18.7 mg |
| total | 398.3 mg |

Formulation Example 11

(1) Compound A (85.36 g), amlodipine besylate (13.87 g), mannitol (184.89 g) and crystalline cellulose (22.5 g) were uniformly mixed in a fluid bed granulator (Lab-1, POWREX CORPORATION) and granulated by spraying an aqueous solution of hydroxypropylcellulose (12.0 g), fumaric acid (4.0 g) and sodium hydroxide (1.38 g), and then dried in the fluid bed granulator. The obtained granules were passed through 16 mesh sieves (aperture 1.0 mm) to give sieved granules A. Croscarmellose sodium (25.6 g), crystalline cellulose (32.0 g), magnesium stearate (3.2 g) and the sieved granules were mixed in a polyethylene bag.

(2) The obtained mixed granules were tableted by a rotary tableting machine (VEL50306SS2MZ, Kikusui Seisakusho, Ltd.) using a 9.5 mmφ punch (tableting pressure: 7 KN/punch, weight per tablet: 400 mg) to give plain tablets having the following composition. Then, the plain tablets were dried under the reduced pressure at 40° C. for 16 hr.

| composition of preparation (per 400 mg) | |
|---|---|
| compound A | 85.36 mg |
| amlodipine besylate | 13.87 mg |
| mannitol | 184.89 mg |
| crystalline cellulose | 22.5 mg |
| hydroxypropylmethylcellulose | 12 mg |
| fumaric acid | 4 mg |
| sodium hydroxide | 1.38 mg |
| croscarmellose sodium | 40 mg |
| crystalline cellulose | 32 mg |
| magnesium stearate | 4 mg |
| total | 400 mg |

Formulation Example 12

(1) Amlodipine besylate (41.61 g), crystalline cellulose (35.1 g) and mannitol (349.89 g) were uniformly mixed in a fluid bed granulator (Lab-1, POWREX CORPORATION) and granulated by spraying an aqueous solution of hydroxypropylmethylcellulose (16.2 g), and then dried in the fluid bed granulator. The obtained granules were passed through 16 mesh sieves (aperture 1.0 mm) to give sieved granules A. Croscarmellose sodium (15.12 g), crystalline cellulose (21.6 g), magnesium stearate (2.16 g) and the sieved granules (177.12 g) were mixed in a polyethylene bag to give mixed granules A.

(2) Compound A (136.58 g) and mannitol (306.98 g) were uniformly mixed in a fluid bed granulator (Lab-1, POWREX CORPORATION) and granulated by spraying an aqueous solution of hydroxypropylcellulose (17.3 g), fumaric acid (6.4 g) and sodium hydroxide (2.21 g), and then dried in the fluid bed granulator. The obtained granules were passed through 16 mesh sieves (aperture 1.0 mm) to give sieved granules B. Croscarmellose sodium (32.4 g), crystalline cellulose (43.2 g), magnesium stearate (4.3 g) and the sieved granules (352.1 g) were mixed in a polyethylene bag to give mixed granules B.

(3) The obtained mixed granules A (180 mg) and B (360 mg) were tableted with an Autograph (manufactured by Shimadzu Corporation, AG-5000B) using a 11 mmϕ punch (tableting pressure: 9 KN/punch, weight per tablet: 540 mg) to give plain tablets having the following composition. Then, the plain tablets were dried under the reduced pressure at 40° C. for 16 hr.

| composition of preparation (per 540 mg) | |
| --- | --- |
| compound A | 85.36 mg |
| amlodipine besylate | 13.87 mg |
| mannitol | 308.49 mg |
| crystalline cellulose | 11.7 mg |
| hydroxypropylcellulose | 10.8 mg |
| hydroxypropylmethylcellulose | 5.4 mg |
| fumaric acid | 4 mg |
| sodium hydroxide | 1.38 mg |
| croscarmellose sodium | 39.6 mg |
| crystalline cellulose | 54 mg |
| magnesium stearate | 5.4 mg |
| total | 540 mg |

Comparative Example 1

Compound A (42.68 g), lactose (217.32 g), and crystalline cellulose (32 g) were uniformly mixed in a fluid bed granulator (Lab-1, POWREX CORPORATION) and granulated by spraying an aqueous solution of hydroxypropylcellulose (12 g) and then dried in the fluid bed granulator. The obtained granules were passed through 16 mesh sieves (aperture 1.0 mm) to give sieved granules. Low-substituted hydroxypropylcellulose (0.8 g) and the sieved granules (15.2 g) was mixed in a glass bottle. The obtained mixed granules were tableted with an Autograph (manufactured by Shimadzu Corporation, AG-5000B) using a 9.5 mmϕ punch (tableting pressure: 7.5 KN/punch, weight per tablet: 374.9 mg) to give plain tablets having the following composition. Then, the plain tablets were dried the under reduced pressure at 40° C. for 16 hr.

| composition of preparation (per 374.9 mg) | |
| --- | --- |
| compound A | 50 mg |
| lactose | 254.6 mg |
| crystalline cellulose | 37.5 mg |
| hydroxypropylcellulose | 14.1 mg |
| low-substituted hydroxypropylcellulose | 18.7 mg |
| total | 374.9 mg |

Formulation Example 13

(1) Compound A (136.58 g) and mannitol (306.98 g) were uniformly mixed in a fluid bed granulator (Lab-1, POWREX CORPORATION) and granulated by spraying an aqueous solution of hydroxypropylcellulose (17.3 g), fumaric acid (6.4 g) and sodium hydroxide (2.21 g), and then dried in the fluid bed granulator. The obtained granules were passed through 16 mesh sieves (aperture 1.0 mm) to give sieved granules A. Croscarmellose sodium (32.4 g), crystalline cellulose (43.2 g), magnesium stearate (4.3 g) and the sieved granules A (352.1 g) were mixed in a polyethylene bag to give mixed granules A.

(2) Crystalline cellulose (spheres) (212.5 g) was charged in a rotary granulator (SPIR-A-FLOW, Freund Corporation), a liquid suspension of amlodipine besylate (34.675 g), crystalline cellulose (7.825 g), low-substituted hydroxypropylcellulose (15 g) and hydroxypropylmethylcellulose (30 g) were sprayed to spheres for layering, and the layered spheres were dried in the rotary granulator. The obtained fine granules were passed through sieves to give 150-350 μm fine granules B.

(3) Low-substituted hydroxypropylcellulose (18 g), hydroxypropylmethylcellulose (25.2 g), talc (10.8 g), titanium oxide (10.8 g) and mannitol (25.2 g) were dissolved and dispersed in purified water (810 g) to give the liquid dispersion. The obtained fine granules B (180 g) was coated in a rotary granulator (SPIR-A-FLOW, Freund Corporation) until the total weight increased by 50%, and dried in the rotary granulator. The obtained fine granules were passed through sieves to give 150-425 μm fine granules C.

(4) The mixed granules A (126 g) and fine granules C (63 g) were mixed in a polyethylene bag. The obtained mixed granules were tableted with a rotary tableting machine (VEL50306SS2MZ, Kikusui Seisakusho, Ltd.) with a 10.5 mmϕ punch (tableting pressure: 8.5 KN/punch, tablet weight per tablet: 540 mg) to give plain tablets with the following composition. Then, the plain tablets were dried under the reduced pressure at 40° C. for 16 hr.

| composition of preparation (per 540 mg) | |
| --- | --- |
| compound A | 85.36 mg |
| mannitol | 191.86 mg |
| hydroxypropylcellulose | 10.8 mg |
| fumaric acid | 4 mg |
| sodium hydroxide | 1.38 mg |
| amlodipine besylate | 13.87 mg |
| crystalline cellulose (spheres) | 85 mg |
| crystalline cellulose | 3.13 mg |
| low-substituted hydroxypropylcellulose | 18 mg |
| hydroxypropylmethylcellulose | 28.8 mg |
| talc | 7.2 mg |
| titanium oxide | 7.2 mg |
| mannitol | 16.8 mg |
| croscarmellose sodium | 27 mg |
| crystalline cellulose | 36 mg |
| magnesium stearate | 3.6 mg |
| total | 540 mg |

Formulation Example 14

(1) Hydroxypropylcellulose (2802 g) was dissolved in purified water (43900 g) to give binder liquid I. Amlodipine besylate (5464 g), mannitol (52860 g) and crystalline cellulose (3870 g) were uniformly mixed in a fluid bed granulator (WSG-60, POWREX CORPORATION) and granulated by spraying the binder liquid I (38700 g) and then dried to give granules. A part of the obtained granules was milled in a powermill grinder (P-7S, Showa Chemical Machinery) with 1.5 mmϕ punching screen to give milled granules. Crystalline cellulose (7290 g), crospovidone (3645 g), magnesium stearate (729 g) and the milled granules were mixed in a tumbler mixer (TM-400S, Showa Chemical Machinery) to give mixed granules A.

(2) Sodium hydroxide (2.76 g) and fumaric acid (8 g) were dissolved in purified water (260 g) to give a buffer solution. Hydroxypropylcellulose (16.2 g) was dissolved in a part thereof (203.1 g) to give binder liquid II. Compound A (128 g), mannitol (260.8 g) and crystalline cellulose (27 g) were uniformly mixed in a fluid bed granulator (Lab-1, POWREX CORPORATION) and granulated by spraying binder liquid II, and then dried to give granules. A part of the obtained granules was passed through 16 mesh sieves (aperture 1.0 mm) to give sieved granules. Crystalline cellulose (36 g), crospovidone (27 g), magnesium stearate (3.6 g) and the sieved granules (293.4 g) were mixed in a polyethylene bag to give mixed granules B'.

(3) The mixed granules A (180 mg) and the mixed granules B' (360 mg) were tableted in the form of a bi-layer using Autograph (AG-500B, manufactured by Shimadzu Corporation) with a major axis 14 mm, a miner axis 8 mmφ punch (tableting pressure 8 KN, weight per tablet: 540 mg) to give plain tablets. Then the plain tablets were dried under the reduced pressure at 40° C. for 15 hr.

| composition of preparation (per 540 mg) | |
|---|---|
| amlodipine besylate | 13.87 mg |
| mannitol | 122.93 mg |
| crystalline cellulose | 9 mg |
| hydroxypropylcellulose | 5.4 mg |
| crystalline cellulose | 18 mg |
| crospovidone | 9 mg |
| magnesium stearate | 1.8 mg |
| compound A | 85.36 mg |
| mannitol | 173.86 mg |
| crystalline cellulose | 18 mg |
| sodium hydroxide | 1.38 mg |
| fumaric acid | 4 mg |
| hydroxypropylcellulose | 10.8 mg |
| crystalline cellulose | 36 mg |
| crospovidone | 27 mg |
| magnesium stearate | 3.6 mg |
| total | 540 mg |

Comparative Example 2

(1) Hydroxypropylcellulose (2802 g) was dissolved in purified water (43900 g) to give binder liquid I. Amlodipine besylate (5464 g), mannitol (52860 g) and crystalline cellulose (3870 g) were uniformly mixed in a fluid bed granulator (WSG-60, POWREX CORPORATION) and granulated by spraying the binder liquid I (38700 g) and then dried to give granules. A part of the obtained granules was milled in a powermill grinder (P-7S, Showa Chemical Machinery) with 1.5 mmφ punching screen to give milled granules. Crystalline cellulose (7290 g), crospovidone (3645 g), magnesium stearate (729 g) and the milled granules (61240 g) were mixed in a tumbler mixer (TM-400S, Showa Chemical Machinery) to give mixed granules A.

(2) Hydroxypropylcellulose (16.2 g) was dissolved in purified water (253.8 g) to give binder liquid II. Compound A (128 g), mannitol (268.9 g) and crystalline cellulose (27 g) were uniformly mixed in a fluid bed granulator (Lab-1, POWREX CORPORATION) and granulated by spraying binder liquid II, and then dried to give granules. A part of the obtained granules was passed through 16 mesh sieves (aperture 1.0 mm) to give sieved granules. Crystalline cellulose (36 g), crospovidone (27 g), magnesium stearate (3.6 g) and the sieved granules (293.4 g) were mixed in a polyethylene bag to give mixed granules B.

(3) The mixed granules A (180 mg) and the mixed granules B (360 mg) were tableted in the form of a bi-layer using Autograph (AG-500B, manufactured by Shimadzu Corporation) with a punch having a major axis 14 mm, a miner axis 8 mmφ (tableting pressure 8 KN, weight per tablet: 540 mg) to give plain tablets. Then the plain tablets were dried under the reduced pressure at 40° C. for 15 hr.

| composition of preparation (per 540 mg) | |
|---|---|
| amlodipine besylate | 13.87 mg |
| mannitol | 122.93 mg |
| crystalline cellulose | 9 mg |
| hydroxypropylcellulose | 5.4 mg |
| crystalline cellulose | 18 mg |
| crospovidone | 9 mg |
| magnesium stearate | 1.8 mg |
| compound A | 85.36 mg |
| mannitol | 179.24 mg |
| crystalline cellulose | 18 mg |
| hydroxypropylcellulose | 10.8 mg |
| crystalline cellulose | 36 mg |
| crospovidone | 27 mg |
| magnesium stearate | 3.6 mg |
| total | 540 mg |

Formulation Example 15

(1) Hydroxypropylcellulose (2802 g) was dissolved in purified water (43900 g) to give binder liquid I. Amlodipine besylate (2982 g), mannitol (55840 g) and crystalline cellulose (3870 g) were uniformly mixed in a fluid bed granulator (WSG-60, POWREX CORPORATION) and granulated by spraying the binder liquid I (38700 g) and then dried to give granules. A part of the obtained granules was milled in a powermill grinder (P-7S, Showa Chemical Machinery) with 1.5 mmφ punching screen to give milled granules. Crystalline cellulose (7290 g), crospovidone (3645 g), magnesium stearate (729 g) and the milled granules (61240 g) were mixed in a tumbler mixer (TM-400S, Showa Chemical Machinery) to give mixed granules A.

(2) Sodium hydroxide (405.8 g) and fumaric acid (1176 g) were dissolved in purified water (3823 g) to give a buffer solution. Hydroxypropylcellulose (3018 g) was dissolved in purified water (47280 g) to give binder liquid II. Compound A (20060 g), mannitol (40860 g) and crystalline cellulose (4230 g) were uniformly mixed in a fluid bed granulator (WSG-60, POWREX CORPORATION) and granulated by spraying the buffer solution (31810 g) and then the binder liquid II (42300 g), and then dried to give granules. A part of the obtained granules was milled in a powermill grinder (P-7S, Showa Chemical Machinery) with 1.5 mmφ punching screen to give milled granules. Crystalline cellulose (7380 g), crospovidone (5535 g), magnesium stearate (738 g) and the milled granules (60150 g) were mixed in a tumbler mixer (TM-400S, Showa Chemical Machinery) to give mixed granules B.

(3) The mixed granules A (180 mg) and the mixed granules B (180 mg) were tableted in the form of a bi-layer using a rotary tableting machine (HT-CVX54LS-UW/C&3L, HATA IRON WORKS CO., LTD) with a 9.5 mmφ punch (tableting pressure 10 KN, weight per tablet: 360 mg) to give plain tablets.

(4) Hydroxypropylmethylcellulose (3978 g) and talc (612 g) were dissolved in purified water (36720 g) to give dispersion liquid I. Titanium oxide (459 g) and iron oxide (51 g) were dispersed in purified water (9180 g) to give dispersion liquid II. The dispersion liquid II was added to the dispersion liquid I, and they were stirred to give a coating dispersion. Using a pan coating machine (DRC-1200, POWREX CORPORATION), the coating dispersion was sprayed until the weight of the plain tablets obtained in (3) increased by 10 mg per tablet, whereby film-coated tablets having the following composition were obtained. Then, the film-coated tablets were dried under the reduced pressure at 40° C. for 15 hr.

| composition of preparation (per 370 mg) | |
|---|---|
| amlodipine besylate | 6.935 mg |
| mannitol | 129.865 mg |
| crystalline cellulose | 9 mg |
| hydroxypropylcellulose | 5.4 mg |
| crystalline cellulose | 18 mg |
| crospovidone | 9 mg |
| magnesium stearate | 1.8 mg |
| compound A | 42.68 mg |
| mannitol | 86.93 mg |
| crystalline cellulose | 9 mg |
| sodium hydroxide | 0.69 mg |
| fumaric acid | 2 mg |
| hydroxypropylcellulose | 5.4 mg |
| crystalline cellulose | 18 mg |
| crospovidone | 13.5 mg |
| magnesium stearate | 1.8 mg |
| hydroxypropylmethylcellulose | 7.8 mg |
| talc | 1.2 mg |
| titanium oxide | 0.9 mg |
| iron oxide | 0.1 mg |
| total | 370 mg |

Formulation Example 16

(1) Hydroxypropylcellulose (2802 g) was dissolved in purified water (43900 g) to give binder liquid I. Amlodipine besylate (5964 g), mannitol (52860 g) and crystalline cellulose (3870 g) were uniformly mixed in a fluid bed granulator (WSG-60, POWREX CORPORATION) and granulated by spraying the binder liquid I (38700 g) and then dried to give granules. A part of the obtained granules was milled in a powermill grinder (P-7S, Showa Chemical Machinery) with 1.5 mmϕ punching screen to give milled granules. Crystalline cellulose (7290 g), crospovidone (3645 g), magnesium stearate (729 g) and the milled granules (61240 g) were mixed in a tumbler mixer (TM-400S, Showa Chemical Machinery) to give mixed granules A.

(2) Sodium hydroxide (405.8 g) and fumaric acid (1176 g) were dissolved in purified water (38230 g) to give a buffer solution. Hydroxypropylcellulose (3018 g) was dissolved in purified water (47280 g) to give binder liquid II. Compound A (20060 g), mannitol (40860 g), crystalline cellulose (4230 g) were uniformly mixed in a fluid bed granulator (WSG-60, POWREX CORPORATION) and granulated by spraying the buffer solution (31810 g) and then the binder liquid II (42300 g), and then dried to give granules. A part of the obtained granules was milled in a powermill grinder (P-7S, Showa Chemical Machinery) with 1.5 mmϕ punching screen to give milled granules. Crystalline cellulose (7380 g), crospovidone (5535 g), magnesium stearate (738 g) and the milled granules (60150 g) were mixed in a tumbler mixer (TM-400S, Showa Chemical Machinery) to give mixed granules B.

(3) The mixed granules A (180 mg) and the mixed granules B (180 mg) were tableted in the form of a bi-layer using a rotary tableting machine (HT-CVX54LS-UW/C&3L, HATA IRON WORKS CO., LTD) with a 9.5 mmϕ punch (tableting pressure 10 KN, weight per tablet: 360 mg) to give plain tablets.

(4) Hydroxypropylmethylcellulose (3978 g) and talc (612 g) were dissolved and dispersed in purified water (36720 g) to give dispersion liquid I. Titanium oxide (459 g) and iron oxide (51 g) were dispersed in purified water (9180 g) to give dispersion liquid II. The dispersion liquid II was added to the dispersion liquid I, and they were stirred to give a coating dispersion. Using a pan coating machine (DRC-1200, POWREX CORPORATION), the coating dispersion was sprayed until the weight of the plain tablets obtained in (3) increased by 10 mg per tablet, whereby film-coated tablets having the following composition were obtained. Then, the film-coated tablets were dried under the reduced pressure at 40° C. for 15 hr.

| composition of preparation (per 370 mg) | |
|---|---|
| amlodipine besylate | 13.87 mg |
| mannitol | 122.93 mg |
| crystalline cellulose | 9 mg |
| hydroxypropylcellulose | 5.4 mg |
| crystalline cellulose | 18 mg |
| crospovidone | 9 mg |
| magnesium stearate | 1.8 mg |
| compound A | 42.68 mg |
| mannitol | 86.93 mg |
| crystalline cellulose | 9 mg |
| sodium hydroxide | 0.69 mg |
| fumaric acid | 2 mg |
| hydroxypropylcellulose | 5.4 mg |
| crystalline cellulose | 18 mg |
| crospovidone | 13.5 mg |
| magnesium stearate | 1.8 mg |
| hydroxypropylmethylcellulose | 7.8 mg |
| talc | 1.2 mg |
| titanium oxide | 0.9 mg |
| iron oxide | 0.1 mg |
| total | 370 mg |

Formulation Example 17

(1) Hydroxypropylcellulose (2802 g) is dissolved in purified water (43900 g) to give binder liquid I. Amlodipine besylate (2982 g), mannitol (55840 g) and crystalline cellulose (3870 g) are uniformly mixed in a fluid bed granulator (WSG-60, POWREX CORPORATION) and granulated by spraying the binder liquid I (38700 g) and then dried to give granules. A part of the obtained granules is milled in a powermill grinder (P-7S, Showa Chemical Machinery) with 1.5 mmϕ punching screen to give milled granules. Crystalline cellulose (7290 g), crospovidone (3645 g), magnesium stearate (729 g) and the milled granules (61240 g) are mixed in a tumbler mixer (TM-400S, Showa Chemical Machinery) to give mixed granules A.

(2) Sodium hydroxide (405.8 g) and fumaric acid (1176 g) are dissolved in purified water (38230 g) to give a buffer solution. Hydroxypropylcellulose (3018 g) is dissolved in purified water (47280 g) to give binder liquid II. Compound A (20060 g), mannitol (40860 g) and crystalline cellulose (4230 g) are uniformly mixed in a fluid bed granulator (WSG-60, POWREX CORPORATION) and granulated by spraying the buffer solution (31810 g) and then the binder liquid II (42300 g), and then dried to give granules. A part of the obtained granules is milled in a powermill grinder (P-7S, Showa Chemical Machinery) with 1.5 mmφ punching screen to give milled granules. Crystalline cellulose (7380 g), crospovidone (5535 g), magnesium stearate (738 g) and the milled granules (60150 g) are mixed in a tumbler mixer (TM-400S, Showa Chemical Machinery) to give mixed granules B.

(3) The mixed granules A (180 mg) and the mixed granules B (90 mg) are tableted in the form of bi-layer using a rotary tableting machine (HT-CVX54LS-UW/C&3L, HATA IRON WORKS CO., LTD) with a 8.5 mmφ punch (tableting pressure 9 KN, weight per tablet: 270 mg) to give plain tablets.

(4) Hydroxypropylmethylcellulose (3978 g) and talc (612 g) are dissolved and dispersed in purified water (36720 g) to give dispersion liquid I. Titanium oxide (494.7 g) and iron oxide (15.3 g) are dispersed in purified water (9180 g) to give dispersion liquid II. The dispersion liquid II is added to the dispersion liquid I, and they are mixed by stirring to give a coating dispersion. Using a pan coating machine (DRC-1200, POWREX CORPORATION), the coating dispersion is sprayed until the weight of the plain tablets obtained in (3) increased by 10 mg per tablet to give film-coated tablets having the following composition. Then, the film-coated tablets are dried under the reduced pressure at 40° C. for 15 hr.

| composition of preparation (per 280 mg) | |
|---|---|
| amlodipine besylate | 6.935 mg |
| mannitol | 129.865 mg |
| crystalline cellulose | 9 mg |
| hydroxypropylcellulose | 5.4 mg |
| crystalline cellulose | 18 mg |
| crospovidone | 9 mg |
| magnesium stearate | 1.8 mg |
| compound A | 21.34 mg |
| mannitol | 43.465 mg |
| crystalline cellulose | 4.5 mg |
| sodium hydroxide | 0.345 mg |
| fumaric acid | 1 mg |
| hydroxypropylcellulose | 2.7 mg |
| crystalline cellulose | 9 mg |
| crospovidone | 6.75 mg |
| magnesium stearate | 0.9 mg |
| hydroxypropylmethylcellulose | 7.8 mg |
| talc | 1.2 mg |
| titanium oxide | 0.97 mg |
| iron oxide | 0.03 mg |
| total | 280 mg |

Formulation Example 18

(1) Hydroxypropylcellulose (2802 g) is dissolved in purified water (43900 g) to give binder liquid I. Amlodipine besylate (2982 g), mannitol (55840 g) and crystalline cellulose (3870 g) are uniformly mixed in a fluid bed granulator (WSG-60, POWREX CORPORATION) and granulated by spraying the binder liquid I (38700 g) and then dried to give granules. A part of the obtained granules is milled in a powermill grinder (P-7S, Showa Chemical Machinery) with 1.5 mmφ punching screen to give milled granules. Crystalline cellulose (7290 g), crospovidone (3645 g), magnesium stearate (729 g) and the milled granules (61240 g) are mixed in a tumbler mixer (TM-400S, Showa Chemical Machinery) to give mixed granules A.

(2) Sodium hydroxide (405.8 g) and fumaric acid (1176 g) are dissolved in purified water (38230 g) to give a buffer solution. Hydroxypropylcellulose (3018 g) is dissolved in purified water (47280 g) to give binder liquid II. Compound A (20060 g), mannitol (40860 g) and crystalline cellulose (4230 g) are uniformly mixed in a fluid bed granulator (WSG-60, POWREX CORPORATION) and granulated by spraying the buffer solution (31810 g) and then the binder liquid II (42300 g), and then dried to give granules. A part of the obtained granules is milled in a powermill grinder (P-7S, Showa Chemical Machinery) with 1.5 mmφ punching screen to give milled granules. Crystalline cellulose (7380 g), crospovidone (5535 g), magnesium stearate (738 g) and the milled granules (60150 g) are mixed in a tumbler mixer (TM-400S, Showa Chemical Machinery) to give mixed granules B.

(3) The mixed granules A (180 mg) and the mixed granules B (180 mg) are tableted in the form of a bi-layer using a rotary tableting machine (HT-CVX54LS-UW/C&3L, HATA IRON WORKS CO., LTD) with a 9.5 mmφ punch (tableting pressure 10 KN, weight per tablet: 360 mg) to, give plain tablets.

(4) Hydroxypropylmethylcellulose (3978 g) and talc (612 g) are dissolved and dispersed in purified water (36720 g) to give dispersion liquid I. Titanium oxide (494.7 g) and iron oxide (15.3 g) are dispersed in purified water (9180 g) to give dispersion liquid II. The dispersion liquid II is added to the dispersion liquid I, and they are mixed by stirring to give a coating dispersion. Using a pan coating machine (DRC-1200, POWREX CORPORATION), the coating dispersion is sprayed until the weight of the plain tablets obtained in (3) increased by 10 mg per tablet to give film-coated tablets having the following composition. Then, the film-coated tablets are dried under the reduced pressure at 40° C. for 15 hr.

| composition of preparation (per 370 mg) | |
|---|---|
| amlodipine besylate | 6.935 mg |
| mannitol | 129.865 mg |
| crystalline cellulose | 9 mg |
| hydroxypropylcellulose | 5.4 mg |
| crystalline cellulose | 18 mg |
| crospovidone | 9 mg |
| magnesium stearate | 1.8 mg |
| compound A | 42.68 mg |
| mannitol | 86.93 mg |
| crystalline cellulose | 9 mg |
| sodium hydroxide | 0.69 mg |
| fumaric acid | 2 mg |
| hydroxypropylcellulose | 5.4 mg |
| crystalline cellulose | 18 mg |
| crospovidone | 13.5 mg |
| magnesium stearate | 1.8 mg |
| hydroxypropylmethylcellulose | 7.8 mg |
| talc | 1.2 mg |
| titanium oxide | 0.97 mg |
| iron oxide | 0.03 mg |
| total | 370 mg |

Formulation Example 19

(1) Hydroxypropylcellulose (2802 g) is dissolved in purified water (43900 g) to give binder liquid I. Amlodipine besylate (2982 g), mannitol (55840 g) and crystalline cellulose (3870 g) are uniformly mixed in a fluid bed granulator (WSG-60, POWREX CORPORATION) and granulated by spraying the binder liquid I (38700 g) and then dried to give granules. A part of the obtained granules is milled in a powermill grinder (P-7S, Showa Chemical Machinery) with 1.5 mmφ punching screen to give milled granules. Crystalline cellulose (7290 g), crospovidone (3645 g), magnesium stearate (729 g) and the milled granules (61240 g) are mixed in a tumbler mixer (TM-400S, Showa Chemical Machinery) to give mixed granules A.

(2) Sodium hydroxide (405.8 g) and fumaric acid (1176 g) are dissolved in purified water (38230 g) to give a buffer solution. Hydroxypropylcellulose (3018 g) is dissolved in purified water (47280 g) to give binder liquid II. Compound A (20060 g), mannitol (40860 g) and crystalline cellulose (4230 g) are uniformly mixed in a fluid bed granulator (WSG-60, POWREX CORPORATION) and granulated by spraying the buffer solution (31810 g) and then the binder liquid II (42300 g), and then dried to give granules. A part of the obtained granules is milled in a powermill grinder (P-7S, Showa Chemical Machinery) with 1.5 mmφ punching screen to give milled granules. Crystalline cellulose (7380 g), crospovidone (5535 g), magnesium stearate (738 g) and the milled granules are mixed in a tumbler mixer (TM-400S, Showa Chemical Machinery) to give mixed granules B.

(3) The mixed granules A (180 mg) and the mixed granules B (360 mg) are tableted in the form of a bi-layer using a rotary tableting machine (HT-CVX54LS-UW/C&3L, HATA IRON WORKS CO., LTD) with a punch having a major axis 14 mm, a miner axis 8 mm (tableting pressure 11 KN, weight per tablet: 540 mg) to give plain tablets.

(4) Hydroxypropylmethylcellulose (3978 g) and talc (612 g) are dissolved and dispersed in purified water (36720 g) to give dispersion liquid I. Titanium oxide (494.7 g), iron oxide (15.3 g) are dispersed in purified water (9180 g) to give dispersion liquid II. The dispersion liquid II is added to the dispersion liquid I, and they are mixed by stirring to give a coating dispersion. Using a pan coating machine (DRC-1200, POWREX CORPORATION), the coating dispersion is sprayed until the weight of the plain tablets obtained in (3) increased by 20 mg per tablet to give film-coated tablets having the following composition. Then, the film-coated tablets are dried under the reduced pressure at 40° C. for 15 hr.

| composition of preparation (per 560 mg) | |
|---|---|
| amlodipine besylate | 6.935 mg |
| mannitol | 129.865 mg |
| crystalline cellulose | 9 mg |
| hydroxypropylcellulose | 5.4 mg |
| crystalline cellulose | 18 mg |
| crospovidone | 9 mg |
| magnesium stearate | 1.8 mg |
| compound A | 85.36 mg |
| mannitol | 173.86 mg |
| crystalline cellulose | 18 mg |
| sodium hydroxide | 1.38 mg |
| fumaric acid | 4 mg |
| hydroxypropylcellulose | 10.8 mg |
| crystalline cellulose | 36 mg |
| crospovidone | 27 mg |
| magnesium stearate | 3.6 mg |
| hydroxypropylmethylcellulose | 15.6 mg |
| talc | 2.4 mg |
| titanium oxide | 1.94 mg |
| iron oxide | 0.06 mg |
| total | 560 mg |

Experimental Example 1

The drug dissolution property of the dried plain tablets (free form of compound A) obtained in Reference Example 1 and Comparative Example 1 was evaluated by a dissolution test (0.5 w/w % sodium dodecyl sulfate-comprising phosphate buffer (pH 6.8), 900 mL, Paddle Method, 50 rpm, 37° C.). The dissolution test was performed according to the Japanese Pharmacopoeia 14th Edition Dissolution Test Method 2 (Paddle Method). The results are shown in FIG. 1, wherein -●- shows the results (dissolution ratio (%) of free form of compound A contained in the dry plain tablet of Reference Example 1) of the dried plain tablet of Reference Example 1 and -○- shows the results (dissolution ratio (%) of free form of compound A contained in the dry plain tablet of Comparative Example 1) of the dried plain tablet of Comparative Example 1.

As shown in FIG. 1, it was demonstrated that addition of a pH control agent improves dissolution property.

Experimental Example 2

The dried plain tablets obtained in Reference Example 1 and Comparative Example 1 were stored in a closed glass bottle with a desiccant at 40° C. for one month. An increase in the amount of decomposed products was measured by the following method.

Compound A was dissolved in an extract at about 1 μg/mL, and the solution was filtered using a non-aqueous filter (0.45 μm) and quantified by high performance liquid column chromatography (HPLC) under the following conditions.

HPLC Conditions
detector: ultraviolet absorption photometer,
measurement wavelength: 240 nm
column: YMC-Pack Pro C18, 5 μm, inner diameter: 4.6 mm,
length: 150 mm
column temperature: 25° C.
  mobile phase(A): 0.05 mol/L phosphate buffer (pH 3.0)/ acetonitrile mixed solution (9:1)
  mobile phase(B): 0.05 mol/L phosphate buffer (pH 3.0)/ acetonitrile mixed solution (3:7)
flow: 1 mL/min
gradient program (linear)

| time (min) | mobile phase (A) (%) | mobile phase (B) (%) |
|---|---|---|
| 0 (injecting) | 100 | 0 |
| 10 | 70 | 30 |
| 90 | 0 | 100 |
| 91 | 100 | 0 |
| 110 (injecting) | 100 | 0 |

The results are shown in Table 1. As shown in Table 1, it was demonstrated that addition of a pH control agent suppresses the decomposition of compound A.

TABLE 1

| preparation | increase (%) in the amount of decomposed products |
|---|---|
| tablet of Reference Example 1 | 1.31 |
| tablet of Comparative Example 1 | 3.83 |

Experimental Example 3

The dried plain tablets obtained in Formulation Example 11 and Formulation Example 12 were stored in a closed glass bottle with a desiccant at 60° C. for 2 weeks. An increase in the amount of decomposed products was measured in the following manner.

Compound A was dissolved in an extract to about 1 μm/mL, filtered through a non-aqueous filter (0.45 μm) and subjected to measurement by high performance liquid column chromatography (HPLC) under the following conditions.

HPLC Conditions
detector: ultraviolet absorption photometer,
measurement wavelength: 237 nm
column: YMC-Pack Pro C18, 5 μm, inner diameter: 4.6 mm,
length: 150 mm
column temperature: 25° C.
    mobile phase (A): 0.05 mol/L phosphate buffer (pH 3.0)
    mobile phase (B): acetonitrile
flow: 1 mL/min
gradient program (linear)

| time (min) | mobile phase (A) (%) | mobile phase (B) (%) |
|---|---|---|
| 0 (injecting) | 80 | 20 |
| 40 | 60 | 40 |
| 70 | 30 | 70 |
| 80 | 30 | 70 |
| 81 | 80 | 20 |
| 90 (injecting) | 80 | 20 |

The results are shown in Table 2. As shown in Table 2, it was demonstrated that granulation of each compound suppresses the decomposition of compound A.

TABLE 2

| preparation | increase (%) in the amount of decomposed products |
|---|---|
| tablet of Formulation Example 11 | 5.45 |
| tablet of Formulation Example 12 | 2.78 |

Experimental Example 4

The drug dissolution property of the dried plain tablets (free form of compound A) obtained in Formulation Example 14% and Comparative Example 2 was evaluated according to a method similar to that in Experimental Example 1. The results are shown in FIG. 2, wherein -●- shows the results (dissolution ratio (%) of free form of compound A contained in the dry plain tablet of Formulation Example 14) of the dried plain tablet of Formulation Example 14 and -○- shows the results (dissolution ratio (%) of free form of compound A contained in the dry plain tablet of Comparative Example 2) of the dried plain tablet of Comparative Example 2

Figure 2:
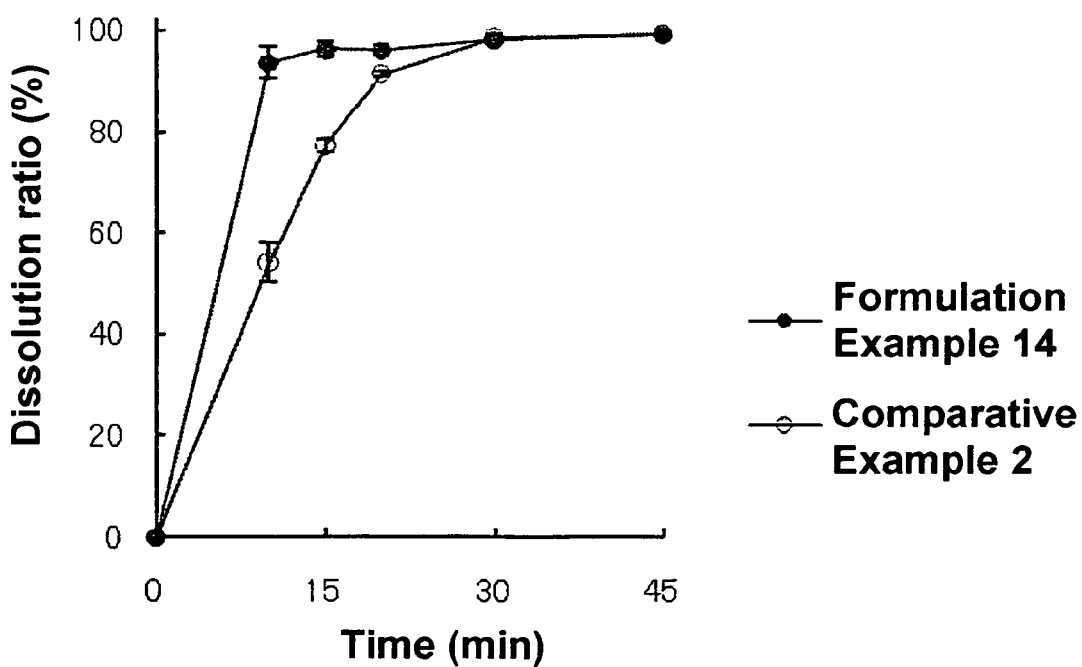
FIG. 2 shows the drug dissolution ratios of tablets obtained in Formulation Example 14 and Comparative Example 2.

As shown in FIG. 2, it was demonstrated that addition of a pH control agent improves dissolution property.

Experimental Example 5

The dried plain tablets obtained in Formulation Example 14 and Comparative Example 2 were stored in a closed glass bottle with a desiccant at 60° C. for 2 weeks. An increase in the amount of decomposed products was measured in the following manner.

Compound A was dissolved in an extract to about 1.6 mg/mL, filtered through a non-aqueous filter (0.45 μm) and subjected to measurement by high performance liquid column chromatography (HPLC) under the following conditions.

HPLC Conditions
detector: ultraviolet absorption photometer,
measurement wavelength: 240 nm
column: YMC-Pack Pro C18, 5 μm, inner diameter: 4.6 mm,
length: 250 mm
column temperature: 25° C.
    mobile phase (A): 0.05 mol/L phosphate buffer (pH 3.0)/acetonitrile mixed solution (4:1)
    mobile phase (B): 0.05 mol/L phosphate buffer (pH 3.0)/acetonitrile mixed solution (3:7)
flow: 1 mL/min
gradient program (linear)

| time (min) | mobile phase (A) (%) | mobile phase (B) (%) |
|---|---|---|
| 0 (injecting) | 85 | 15 |
| 20 | 85 | 15 |
| 90 | 0 | 100 |
| 91 | 85 | 15 |
| 100 (injecting) | 85 | 15 |

The results are shown in Table 3. As shown in Table 3, it was demonstrated that addition of a pH control agent suppresses the decomposition of compound A.

TABLE 3

| preparation | increase (%) in the amount of decomposed products |
|---|---|
| tablet of Formulation Example 14 | 2.15 |
| tablet of Comparative Example 2 | 2.55 |

INDUSTRIAL APPLICABILITY

The present invention is advantageous in that a solid preparation superior in the dissolution property, stability and the like of compound (I) can be provided. In addition, the present invention advantageously provides a solid preparation containing a combination of compound (I) and a calcium antagonist, which is superior in the stability of compound (I) and a calcium antagonist.

While some of the embodiments of the present invention have been described in detail in the above, those of ordinary skill in the art can enter various modifications and changes to the particular embodiments shown without substantially departing from the novel teaching and advantages of the present invention. Such modifications and changes are encompassed in the spirit and scope of the present invention as set forth in the appended claims.

The invention claimed is:
1. A solid oral preparation comprising (a) a first part comprising a compound, which is (5-methyl-2-oxo-1,3-dioxol-4-yl)methyl 2-ethoxy-1-{[2'-(5-oxo-4,5-dihydro-1,2,4-oxadia- zol-3-yl)biphenyl-4-yl]methyl}-1H-benzimidazole-7-carboxylate potassium salt, and a solid pH control agent which is a combination of fumaric acid and a sodium ion donor, wherein the pH control agent provides a pH of 2 to 5 when dissolved or suspended in water at a concentration of 1% w/v at 25° C., the pH control agent is contained in a proportion of 0.1-5 wt % of the preparation, and (b) a second part comprising amlodipine besylate, wherein the first part and the second part are individually granulated, and wherein the solid oral preparation is a multi-layer tablet having (i) a first layer comprised of the first part, and (ii) a second layer comprised of the second part.

* * * * *